(12) United States Patent
Cynader et al.

(10) Patent No.: US 9,458,437 B2
(45) Date of Patent: Oct. 4, 2016

(54) NEUROPROTECTIVE PEPTIDES THAT INHIBIT INTERACTION BETWEEN PALMITOYL ACYL TRANSFERASE ZINC-FINGER DHHC TYPE CONTAINING 17 (ZD17) AND C-JUN N-TERMINAL KINASE (JNK)

(75) Inventors: Max S. Cynader, West Vancouver (CA); Guang Yang, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 0 days.

(21) Appl. No.: 14/232,268

(22) PCT Filed: Jul. 12, 2012

(86) PCT No.: PCT/CA2012/050483
§ 371 (c)(1),
(2), (4) Date: Apr. 2, 2015

(87) PCT Pub. No.: WO2013/006978
PCT Pub. Date: Jan. 17, 2013

(65) Prior Publication Data
US 2015/0225704 A1     Aug. 13, 2015

Related U.S. Application Data

(60) Provisional application No. 61/507,060, filed on Jul. 12, 2011.

(51) Int. Cl.
*A61K 38/45* (2006.01)
*C07K 19/00* (2006.01)
*C12N 9/10* (2006.01)
*A61K 47/48* (2006.01)
*A61K 38/00* (2006.01)

(52) U.S. Cl.
CPC ............ *C12N 9/1029* (2013.01); *A61K 38/45* (2013.01); *A61K 47/48315* (2013.01); *A61K 38/00* (2013.01); *C07K 2319/10* (2013.01); *C07K 2319/23* (2013.01); *C07K 2319/41* (2013.01); *C07K 2319/70* (2013.01)

(58) Field of Classification Search
None
See application file for complete search history.

(56) References Cited

PUBLICATIONS

Aarts M. et al. Treatment of ischemic brain damage by perturbing NMDA receptor—PSD-95 protein interactions. Science (2002) 298:846-850.
Borsello T. & Forloni G. JNK signalling: a possible target to prevent neurodegeneration. Curr Pharm Des (2007) 13:1875-1886.
Borsello T. et al. A peptide inhibitor of c-Jun N-terminal kinase protects against excitotoxicity and cerebral ischemia. Nature Medicine (2003) 9:1180-1186.
Centeno C. et al. Role of the JNK pathway in NMDA-mediated excitotoxicity of cortical neurons. Cell Death Differ (2007) 14:240-253.
Ducker, C.E. et al. Huntingtin interacting protein 14 is an oncogenic human protein: palmitoyl acyltransferase. Oncogene (2004) 23:9230-9237.
El-Husseini Ael D. et al. Synaptic strength regulated by palmitate cycling on PSD-95. Cell (2002) 108, 849-863.
Gao T. et al. Proteins (2009) 76(3):772-777.
Goytain A. et al. Journal of Biological Chemistry (2008) 283(48):33365-33374.
Harada T. et al. AKRL1 and AKRL2 activate the JNK pathway Genes to Cells (2003) 8(5):493-500.
Huang K. et al. Huntingtin-interacting protein HIP14 is a palmitoyl transferase involved in palmitoylation and trafficking of multiple neuronal proteins. Neuron (2004) 44:977-986.
Huang K. et al. Neuronal palmitoyl acyl transferases exhibit distinct substrate specificity. FASEB J (2009) 23, 2605-2615.
Kang R. et al. Neural palmitoyl-proteomics reveals dynamic synaptic palmitoylation. Nature (2008) 456:904-909.
Khatlani T.S. et al. c-Jun N-terminal kinase is activated in non-small-cell lung cancer and promotes neoplastic transformation in human bronchial epithelial cells. Oncogene (2007) 26:2658-2666.
Kornau H.C. et al. Domain interaction between NMDA receptor subunits and the postsynaptic density protein PSD-95. Science (1995) 269:1737-1740.
Kuan C.Y. & Burke R.E. Targetting the JNK signaling pathway for stroke and Parkinson's diseases therapy. Curr Drug Targets CNS Neurol Disord (2005) 4:63-67.
Luttrell L. M., et al. The role of beta-arrestins in the termination of G-protein-coupled receptor signals. Journal of Cell Science 115, 455-465 (2002)
McDonald P.H. et al. Beta-arrestin 2: a receptor-regulated MAPK scaffold for the activation of JNK3. Science (2000) 290:1574-1577.
Merritt S.E. et al. The mixed lineage kinase DLK utilizes MKK7 and not MKK4 as substrate. J Biol Chem (1999) 274:10195-10202.
Minamide L.S. et al. Neurodegenerative stimuli induce persistent ADF/cofilin-actin rods that disrupt distal neurite function. Nat Cell Biol (2000) 2:628-636.

(Continued)

*Primary Examiner* — John Ulm
(74) *Attorney, Agent, or Firm* — Gilbert's LLP; Matthew D. Powell

(57) ABSTRACT

Isolated polypeptides are disclosed herein, the isolated polypeptides comprising at least 90% identity to any one of: SEQ ID NO:1; SEQ ID NO:2; or SEQ ID NO:3, wherein the isolated polypeptide inhibits an interaction between palmitoyl acyl transferase zinc-finger DHHC type containing 17 (z D17) and c-jun N-terminal kinase (JNK). The polypeptides may be conjugated to a delivery and targeting moiety, such as the cell-membrane transduction domain of the HIV-1 Tat protein. There are also provided methods for treating a disease associated with cytotoxicity or excitotoxicity.

14 Claims, 19 Drawing Sheets

(56) References Cited

PUBLICATIONS

Nagel S. et al. Neuroprotection by dimethyloxalylglycine following permanent and transient focal cerebral ischemia in rats. J Cereb Blood Flow Metab. (2011) 31(1):132-43. Epub Apr. 21, 2010.
Olivia AA, Jr., Atkins CM, Copenagle L, Banker GA (2006) Activated c-Jun N-terminal kinase is required for axon formation. J Neurosci 26:9462-9470.
Schwarze S.R. In vivo protein transduction: delivery of a biologically active protein into the mouse. Science (1999) 285:1569-1572.
Singaraja R.R. et al. HIP14, a novel ankyrin domain-containing protein, links huntingtin to intracellular trafficking and endocytosis. Hum Mol Genet (2002) 11, 2815-2828.
Song X. et al. Visual and both non-visual arrestins in their "inactive" conformation bind JNK3 and Mdm2 and relocalize them from the nucleus to the cytoplasm. J Biol Chem (2006) 281:21491-21499.
Tsuruta F. et al. JNK promotes Bax translocation to mitochondria through phosphorylation of 14-3-3 proteins. EMBO J (2004) 23:1889-1899.
Watanabe T. et al. Postischemic intraventricular administration of FGF-2 expressing adenoviral vectors improves neurologic outcome and reduces infarct volume after transient focal cerebral ischemia in rats. J Cereb Blood Flow Metab (2004) 24:1205-1213.
Weston C.R. & Davis R.J. The JNK signal transduction pathway. Curr Opin Cell Biol (2007) 19:142-149.
Weston, C.R. and Davis, D.J., The JNK signal transduction pathway. Current Opinion in Genetics & Development 2002, 12:14-21.
Yanai A., et al. Palmitoylation of huntingtin by HIP14 is essential for its trafficking and function. Nat Neurosci (2006) 9:824-831.
Yang G. and Cynader M.S. The Journal of Neuroscience (2011) 31(33):11980-11991.
Yang G. et al. Subunit-selective palmitoylation regulates the intracellular trafficking of AMPA receptor. Eur J Neurosci (2009) 30:35-46.

A

B

A

B

C

SEQUENCE LISTING

<160> NUMBER OF SEQ ID NOS: 14

<210> SEQ ID NO 1
<211> LENGTH: 20
<212> TYPE: PRT
<213> ORGANISM: Homo sapiens

<400> SEQUENCE: 1

Met Thr Pro Leu Met Trp Ala Ala Tyr Arg Thr His Ser Val Asp Pro
1               5                   10                  15

Thr Arg Leu Leu
            20

<210> SEQ ID NO 2
<211> LENGTH: 10
<212> TYPE: PRT
<213> ORGANISM: Homo sapiens

<400> SEQUENCE: 2

Trp Ala Ala Tyr Arg Thr His Ser Val Asp
1               5                   10

<210> SEQ ID NO 3
<211> LENGTH: 15
<212> TYPE: PRT
<213> ORGANISM: Homo sapiens

<400> SEQUENCE: 3

Thr Pro Leu His Trp Ala Thr Arg Gly Gly His Leu Ser Met Val

```
<210> SEQ ID NO 4
<211> LENGTH: 31
<212> TYPE: PRT
<213> ORGANISM: Artificial Sequence
<220> FEATURE:
<223> OTHER INFORMATION: NIMoE conjugated to TAT protein transduction
      domain (aa 21-31)

<400> SEQUENCE: 4

Met Thr Pro Leu Met Trp Ala Ala Tyr Arg Thr His Ser Val Asp Pro
1               5                   10                  15

Thr Arg Leu Leu Tyr Gly Arg Lys Lys Arg Arg Gln Arg Arg
            20                  25                  30

<210> SEQ ID NO 5
<211> LENGTH: 21
<212> TYPE: PRT
<213> ORGANISM: Artificial Sequence
<220> FEATURE:
<223> OTHER INFORMATION: NIMoEsh conjugated to TAT protein transduction
      domain (aa 11-21)

<400> SEQUENCE: 5

Trp Ala Ala Tyr Arg Thr His Ser Val Asp Tyr Gly Arg Lys Lys Arg
1               5                   10                  15

Arg Gln Arg Arg Arg
            20

<210> SEQ ID NO 6
<211> LENGTH: 26
<212> TYPE: PRT
<213> ORGANISM: Artificial Sequence
<220> FEATURE:
<223> OTHER INFORMATION: NIMoD conjugated to TAT protein transduction
      domain (aa 16-26)

<400> SEQUENCE: 6

Thr Pro Leu His Trp Ala Thr Arg Gly Gly His Leu Ser Met Val Tyr
1               5                   10                  15

Gly Arg Lys Lys Arg Arg Gln Arg Arg Arg
            20                  25

<210> SEQ ID NO 7
<211> LENGTH: 31
<212> TYPE: PRT
<213> ORGANISM: Artificial Sequence
<220> FEATURE:
<223> OTHER INFORMATION: NIMoE conjugated to TAT protein transduction
      domain (aa 1-11)

<400> SEQUENCE: 7

Tyr Gly Arg Lys Lys Arg Arg Gln Arg Arg Arg Met Thr Pro Leu Met
1               5                   10                  15

Trp Ala Ala Tyr Arg Thr His Ser Val Asp Pro Thr Arg Leu Leu
            20                  25                  30

<210> SEQ ID NO 8
<211> LENGTH: 21
<212> TYPE: PRT
<213> ORGANISM: Artificial Sequence
<220> FEATURE:
<223> OTHER INFORMATION: NIMoEsh conjugated to TAT protein transduction
      domain (aa 1-11)
```

```
<400> SEQUENCE: 8

Tyr Gly Arg Lys Lys Arg Arg Gln Arg Arg Trp Ala Ala Tyr Arg
1               5                   10                  15

Thr His Ser Val Asp
            20

<210> SEQ ID NO 9
<211> LENGTH: 26
<212> TYPE: PRT
<213> ORGANISM: Artificial Sequence
<220> FEATURE:
<223> OTHER INFORMATION: NIMoD conjugated to TAT protein transduction
      domain (aa 1-11)

<400> SEQUENCE: 9

Tyr Gly Arg Lys Lys Arg Arg Gln Arg Arg Thr Pro Leu His Trp
1               5                   10                  15

Ala Thr Arg Gly Gly His Leu Ser Met Val
            20                  25

<210> SEQ ID NO 10
<211> LENGTH: 13
<212> TYPE: PRT
<213> ORGANISM: Homo sapiens

<400> SEQUENCE: 10

Asn Val Lys Gly Glu Ser Ala Leu Asp Leu Ala Lys Gln
1               5                   10

<210> SEQ ID NO 11
<211> LENGTH: 20
<212> TYPE: PRT
<213> ORGANISM: Artificial Sequence
<220> FEATURE:
<223> OTHER INFORMATION: NIMoEscr scrambled NIMoE

<400> SEQUENCE: 11

His Arg Tyr Arg Trp Leu Thr Asp Leu Leu Ser Met Val Thr Thr Pro
1               5                   10                  15

Ala Ala Pro Met
            20

<210> SEQ ID NO 12
<211> LENGTH: 20
<212> TYPE: PRT
<213> ORGANISM: Artificial Sequence
<220> FEATURE:
<223> OTHER INFORMATION: NIMoEmut NIMoE sequence with point mutations on
      three charged amino acids at positions 10, 12, and 15

<400> SEQUENCE: 12

Met Thr Pro Leu Met Trp Ala Ala Tyr Gly Thr Gly Ser Val Gly Pro
1               5                   10                  15

Thr Arg Leu Leu
            20

<210> SEQ ID NO 13
<211> LENGTH: 31
<212> TYPE: PRT
<213> ORGANISM: Artificial Sequence
<220> FEATURE:
<223> OTHER INFORMATION: scrambled NIMoE conjugated to TAT protein
      transduction domain (aa 1-11)

<400> SEQUENCE: 13
```

```
Tyr Gly Arg Lys Lys Arg Arg Gln Arg Arg His Arg Tyr Arg Trp
1               5                   10                  15

Leu Thr Asp Leu Leu Ser Met Val Thr Thr Pro Ala Ala Pro Met
                20                  25                  30

<210> SEQ ID NO 14
<211> LENGTH: 31
<212> TYPE: PRT
<213> ORGANISM: Artificial Sequence
<220> FEATURE:
<223> OTHER INFORMATION: NIMoEmut conjugated to TAT protein transduction
      domain (aa 1-11)

<400> SEQUENCE: 14

Tyr Gly Arg Lys Lys Arg Arg Gln Arg Arg Met Thr Pro Leu Met
1               5                   10                  15

Trp Ala Ala Tyr Gly Thr Gly Ser Val Gly Pro Thr Arg Leu Leu
                20                  25                  30
```

US 9,458,437 B2

NEUROPROTECTIVE PEPTIDES THAT INHIBIT INTERACTION BETWEEN PALMITOYL ACYL TRANSFERASE ZINC-FINGER DHHC TYPE CONTAINING 17 (ZD17) AND C-JUN N-TERMINAL KINASE (JNK)

RELATED APPLICATIONS

This application claims priority to U.S. provisional patent application 61/507,060 filed 12 Jul. 2011 and is a national stage of PCT International Patent Application serial no. PCT/CA2012/050483.

FIELD OF THE INVENTION

The invention relates to neuroprotection by targeting stress-induced protein-protein interactions, such as the interaction of palmitoyl acyl transferase zinc-finger DHHC type containing 17 (zD17) and c-jun N-terminal kinase (JNK). In particular, the invention relates to neuroprotection using isolated polypeptides to reduce cytotoxic or excitotoxic stress through inhibition of zD17 and JNK interactions.

BACKGROUND OF THE INVENTION

Excitotoxicity is the pathological process by which nerve cells may be damaged or killed by glutamate and similar substances. Excitotoxicity may be involved in spinal cord injury, stroke, traumatic brain injury and neurodegenerative diseases of the central nervous system (CNS) such as multiple sclerosis, Alzheimer's disease, amyotrophic lateral sclerosis (ALS), Parkinson's disease, alcoholism or alcohol withdrawal and Huntington's disease. Other common conditions that cause excessive glutamate concentrations around neurons are hypoglycemia and status epilepticus.

Stroke may result due to a number of mechanisms. Cerebral thrombosis and cerebral embolism may result from blood clots that block an artery supplying the brain, which are the cause of most strokes. Subarachnoid hemorrhage and intracerebral hemorrhage occur when a blood vessel bursts in or around the brain. Accordingly, strokes may be ischemic (i.e. cerebral thrombosis or cerebral embolism) or hemorrhagic (i.e. subarachnoid hemorrhage or intracerebral hemorrhage) in nature.

A blood clot or thrombus formation is often the result of atherosclerosis of a brain artery. A transient ischemic attack (TIA) is also referred to as a mini-stroke and is characterized by a temporary blood flow interruption and often precedes a stroke.

An embolism occurs when a blood clot becomes dislodged from a remote location in the circulatory system and subsequently becomes lodged in an artery supplying the brain (for example, in the brain or in the neck). Cerebral embolisms often occur in patients with atrial fibrillation, where the upper chambers (atria) of the heart beat weakly and rapidly and the blood in the atria is not completely emptied. The blood which stagnates is more susceptible to clot formation.

A hemorrhage or bleeding, occurs when a blood vessel breaks. A break in a blood vessel may result from trauma or excess internal pressure. The vessels most likely to break are those with preexisting defects such as an aneurysm.

An intracerebral hemorrhage occurs in the vessels of the brain, while subarachnoid hemorrhage affects arteries at the brain's surface (i.e. protective arachnoid membrane).

All of the above stroke mechanisms may result in the death of brain cells, which in turn triggers a chain reaction in which toxic chemicals created by cell death may damage neighbouring cells. Cells in the affected region of the brain often die because they no longer receive oxygen and nutrients from the blood and due to excessive glutamate concentrations, leading to the symptoms and disabilities of stroke patients. Stroke is the third leading cause of death in North America, and the leading cause of disability.

SUMMARY

This invention is based, in part, on the discovery that isolated polypeptides described herein selectively inhibit an interaction between palmitoyl acyl transferase zinc-finger DHHC type containing 17 (zD17) and c-jun N-terminal kinase (JNK). Furthermore, as disclosed herein, the selective inhibition of interaction between zD17 and JNK may be useful in the reducing excitotoxic stress in cells. Excitotoxic stress in cells may be associated with a disease, the disease may be selected from the following without limitation: spinal cord injury, stroke, traumatic brain injury, alcoholism or alcohol withdrawal, and neurodegenerative diseases of the central nervous system (CNS) such as multiple sclerosis, Alzheimer's disease, amyotrophic lateral sclerosis (ALS), Parkinson's disease, and Huntington's disease.

The compounds described herein may be used for in vivo or in vitro research uses (i.e. non-clinical) to investigate alternative treatments for excitotoxic stress or cytotoxic stress. Furthermore, these isolated polypeptides may be used individually or as part of a kit for in vivo or in vitro research to investigate mechanisms of excitotoxic stress or cytotoxic stress using recombinant proteins, nucleotides encoding the isolated polypeptides, cells maintained in culture, and/or animal models.

In one aspect, there is provided an isolated polypeptide comprising at least 80% identity to any one of SEQ ID NO:1 or SEQ ID NO:2 or SEQ ID NO:3. Alternatively, there is provided an isolated polypeptide comprising at least 85% identity to any one of SEQ ID NO:1 or SEQ ID NO:2 or SEQ ID NO:3. Alternatively, there is provided an isolated polypeptide comprising at least 90% identity to any one of SEQ ID NO:1 or SEQ ID NO:2 or SEQ ID NO:3. Alternatively, there is provided an isolated polypeptide comprising at least 95% identity to any one of SEQ ID NO:1 or SEQ ID NO:2 or SEQ ID NO:3. Alternatively, there is provided an isolated polypeptide comprising any one of SEQ ID NO:1 or SEQ ID NO:2 or SEQ ID NO:3.

In another aspect, there is provided an isolated polypeptide having at least 90% identity to any one of: SEQ ID NO:1; SEQ ID NO:2; or SEQ ID NO:3; wherein the identity may be calculated over the length of the sequence, and wherein the isolated polypeptide inhibits an interaction between palmitoyl acyl transferase zinc-finger DHHC type containing 17 (zD17) and c-jun N-terminal kinase (JNK).

In another aspect, there is provided an isolated polypeptide having at least 90% identity to any one of: SEQ ID NO:1; SEQ ID NO:2; or SEQ ID NO:3, wherein the isolated polypeptide inhibits an interaction between palmitoyl acyl transferase zinc-finger DHHC type containing 17 (zD17) and c-jun N-terminal kinase (JNK).

In another aspect, there is provided an isolated polypeptide having at least 95% identity to any one of: SEQ ID NO:1; SEQ ID NO:2; or SEQ ID NO:3, wherein the isolated polypeptide inhibits an interaction between palmitoyl acyl transferase zinc-finger DHHC type containing 17 (zD17) and c-jun N-terminal kinase (JNK).

In another aspect, there is provided an isolated polypeptide comprising any one of: SEQ ID NO:1; SEQ ID NO:2; or SEQ ID NO:3.

The isolated polypeptide may inhibit an interaction between palmitoyl acyl transferase zinc-finger DHHC type containing 17 (zD17) and c-jun N-terminal kinase (JNK). The isolated polypeptide may further include a delivery and targeting moiety conjugated to the isolated polypeptide. The delivery and targeting moiety may be selected from one or more of: ligands; protein transduction domains; or antibodies. The protein transduction domain may be the cell-membrane transduction domain of the HIV-1 Tat protein.

In another aspect, there is provided an isolated polynucleotide, including a series of nucleotides encoding the polypeptide described herein.

In another aspect, there is provided a composition comprising the polypeptide as described herein and a carrier.

The carrier may be a pharmaceutically acceptable carrier.

In another aspect, there is provided a vector comprising an isolated polynucleotide as described herein.

In another aspect, there is provided a cell including the vector as described herein.

In another aspect, there is provided a cell including a polynucleotide as described herein, wherein the polynucleotide may be operably linked to an expression control sequence.

In another aspect, there is provided a method of protecting a cell from excitotoxic stress, the method including delivering an isolated polypeptide as described herein to the cell.

In another aspect, there is provided a method of protecting a cell from excitotoxic stress, the method including: (a) delivering the vector as described herein to the cell; and (b) expressing the polynucleotide carried by the vector.

In another aspect, there is provided a method of expressing a polypeptide, the method including: (a) delivering the vector of as described herein to a cell; and (b) maintaining the cell under conditions permitting expression of the polynucleotide carried by the vector.

The delivering of the vector to the cell may be carried out in vivo. The delivering of the vector to the cell may be carried out ex vivo. The delivering of the vector to the cell may be carried out in vitro.

In another aspect, there is provided a method of treating a disease associated with excitotoxicity, the method including: administering a biologically effective amount of the polypeptide as described herein to a subject in need thereof.

The biologically effective amount may be an amount sufficient to prevent excitotoxicity-induced cell death. The disease associated with excitotoxicity may be selected from spinal cord injury, stroke, brain injury, multiple sclerosis, Alzheimer's disease, amyotrophic lateral sclerosis (ALS), Parkinson's disease, alcoholism or alcohol withdrawal, and Huntington's disease. The disease associated with excitotoxicity may be stroke.

In another aspect, there is provided a pharmaceutical composition for treating a disease associated with excitotoxicity, the composition including an isolated polypeptide as described herein and a pharmaceutically acceptable carrier.

The disease associated with excitotoxicity may be selected from spinal cord injury, stroke, brain injury, multiple sclerosis, Alzheimer's disease, amyotrophic lateral sclerosis (ALS), Parkinson's disease, alcoholism or alcohol withdrawal, and Huntington's disease. The disease associated with excitotoxicity may be stroke.

In another aspect, there is provided a use of an isolated polypeptide as described herein to treat a disease associated with cytotoxicity or excitotoxicity.

In another aspect, there is provided a use of an isolated polypeptide as described herein for preparing a medicament to treat a disease associated with cytotoxicity or excitotoxicity.

The disease associated with excitotoxicity may be selected from spinal cord injury, stroke, brain injury, multiple sclerosis, Alzheimer's disease, amyotrophic lateral sclerosis (ALS), Parkinson's disease, alcoholism or alcohol withdrawal, and Huntington's disease. The disease associated with excitotoxicity may be stroke.

In another aspect, there is provided an isolated polypeptide as described herein n isolated polypeptide for use in treating a disease associated with cytotoxicity or excitotoxicity.

The disease associated with excitotoxicity may be selected from spinal cord injury, stroke, brain injury, multiple sclerosis, Alzheimer's disease, amyotrophic lateral sclerosis (ALS), Parkinson's disease, alcoholism or alcohol withdrawal, and Huntington's disease. The disease associated with excitotoxicity may be stroke.

In another aspect, there is provided a commercial package including: (a) an isolated polypeptide of as described herein; and (b) instructions for the use thereof for treating a disease associated with cytotoxicity or excitotoxicity.

In another aspect, there is provided a commercial package including: (a) an isolated polypeptide described herein and a pharmaceutically acceptable carrier; and (b) instructions for the use thereof for treating a disease associated with cytotoxicity or excitotoxicity.

In another aspect, there is provided a commercial package including: (a) a pharmaceutical composition described herein; and (b) instructions for the use thereof for treating a disease associated with cytotoxicity or excitotoxicity.

The disease associated with excitotoxicity may be selected from spinal cord injury, stroke, brain injury, multiple sclerosis, Alzheimer's disease, amyotrophic lateral sclerosis (ALS), Parkinson's disease, alcoholism or alcohol withdrawal, and Huntington's disease. The disease associated with excitotoxicity may be stroke.

In another aspect, there is provided a pharmaceutical composition including: (a) an isolated polypeptide having at least 90% identity to any one of: SEQ ID NO:1; SEQ ID NO:2; or SEQ ID NO:3; wherein the identity is calculated over the length of the sequence, and wherein the isolated polypeptide inhibits an interaction between palmitoyl acyl transferase zinc-finger DHHC type containing 17 (zD17) and c-jun N-terminal kinase (JNK); and (b) a pharmaceutically acceptable excipient.

The excipient may be an isotonic injection solution. The composition may be suitable for human administration. The isolated polypeptide may be present in a fusion protein comprising a cell-membrane transduction domain of the HIV-1 Tat protein. The pharmaceutical composition may be in a sterile container. The container may be a syringe. The sterile container may be provided in a kit or commercial package.

In another aspect, there is provided an isolated polypeptide as described herein, wherein the isolated polypeptide inhibits stress induced protein-protein interactions (for example, an interaction between palmitoyl acyl transferase zinc-finger DHHC type containing 17 (zD17) and c-jun N-terminal kinase (JNK)). In another aspect, there are provided an isolated polypeptide as described herein, wherein the isolated polypeptide protects cells from cytotoxic stress. The cytotoxic stress may be excitotoxic stress. In another aspect, the isolated polypeptide may further comprise a delivery and targeting moiety conjugated to the isolated polypeptide. Optionally, the delivery and targeting moiety may be selected from one or more of: ligands, protein transduction domains, or antibodies. Optionally, the protein transduction domain may be the cell-membrane transduction domain of the HIV-1 Tat protein (for example, see SEQ ID NOs:4-9).

Other aspects and features of the present invention will become apparent to those ordinarily skilled in the art upon review of the following description of specific embodiments of the invention in conjunction with the accompanying figures.

DETAILED DESCRIPTION

Figure 1:
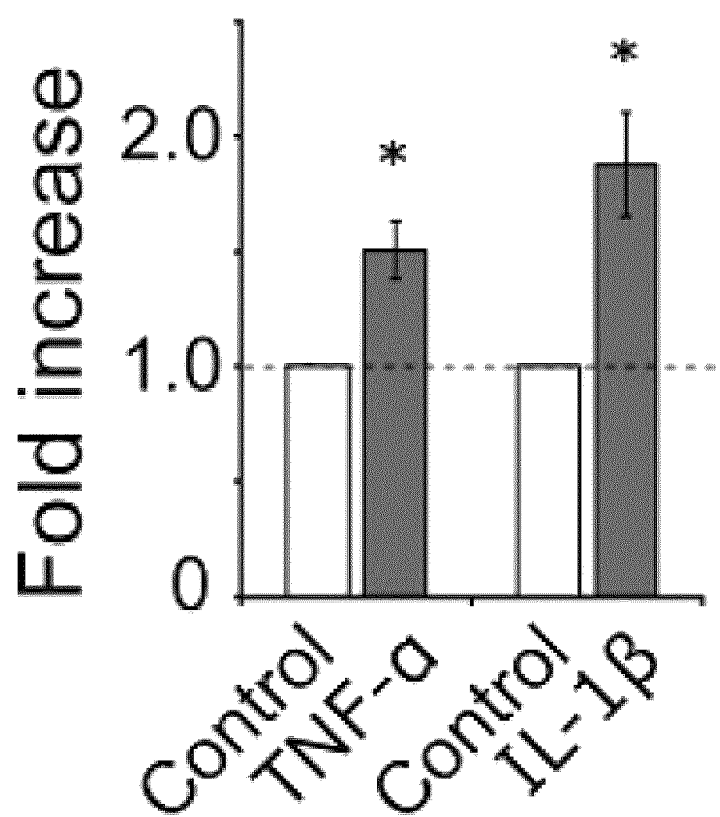
FIG. 1 shows a bar graph of cytokines TNF-α and IL-1β enhance the zD17-JNK3 interaction in neuronal cultures, wherein TNF-α (50 ng/ml, 6 h) and IL-1β (10 ng/ml, 16 h) treatments induced a 1.53±0.11 and 1.88±0.23 fold increase of zD17-JNK3 interaction, respectively.

The term "identity" as used herein refers to the measure of the identity of sequence between two peptides or between two nucleic acids molecules. Identity can be determined by comparing a position in each sequence which may be aligned for purposes of comparison. Two amino acid or nucleic acid sequences are considered substantially identical if they share at least about 80% sequence identity or at least about 81% sequence identity, or at least about 82% sequence identity, or at least about 83% sequence identity, or at least about 84% sequence identity, or at least about 85% sequence identity, or at least about 86% sequence identity, or at least about 87% sequence identity, or at least about 88% sequence identity, or at least about 89% sequence identity, or at least about 90% sequence identity. Alternatively, two amino acid or nucleic acid sequences are considered substantially identical if they share at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity.

Sequence identity may be determined by the BLAST algorithm currently is use and which was originally described in Altschul et al. (1990) J. Mol. Biol. 215:403-410. The BLAST algorithm may be used with the published default settings. When a position in the compared sequence is occupied by the same base or amino acid, the molecules are considered to have shared identity at that position. The degree of identity between sequences is a function of the number of matching positions shared by the sequences and the degree of overlap between the sequences. Furthermore, when considering the degree of identity with SEQ ID NOs:1-3, it is intended that the equivalent number of amino acids be compared to SEQ ID NOs:1-3, respectively. Additional sequences (i.e. other than those corresponding to the 20, 10, or 15 amino acids of SEQ ID NOs:1-3, respectively), are not intended to be considered when determining the degree of identity with SEQ ID NOs:1-3. The sequence identity of a given sequence may be calculated over the length of the reference sequence (i.e. SEQ ID NOs:1-3).

In certain embodiments, there is provided an isolated polypeptide composition having an amino acid composition substantially similar to SEQ ID NO: 1 or SEQ ID NO: 2 or SEQ ID NO:3. Wherein substantially similar is meant to encompass a degree of sequence identity when an equivalent region (i.e. ~20 or 10 or 15 amino acids, respectively) is compared. Furthermore, substantially similar is meant to encompass conservative substitutions and modified amino acids provided that cell protection activity or other activities described herein are maintained.

As used herein, 'peptide' or 'polypeptide' may be used interchangeably, and generally refer to a compound comprised of at least two amino acid residues covalently linked by peptide bonds or modified peptide bonds. However, when specifically used with reference to a specific SEQ ID NO, it is meant to comprise an amino acid sequence of NIMo represented by SEQ ID NOs:1-3 (i.e. MTPLMWAAYRTHSVDPTRLL (NIMoE); WAAYRTHSVD (NIMoEsh); TPLHWATRGGHLSMV (NIMoD)), wherein the polypeptide has cell protective activity. Modified peptide bonds may include for example peptide isosteres (modified peptide bonds) that may provide additional desired properties to the peptide, such as increased half-life. A peptide may comprise at least two amino acids. The amino acids comprising a peptide or polypeptide described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Amino acids are molecules containing an amine group, a carboxylic acid group and a side chain that varies between different amino acids. An amino acid may be in its natural form or it may be a synthetic amino acid. An amino acid may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine, leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide. An amino acid residue may be generally represented by a one-letter or three-letter designation, corresponding to the trivial name of the amino acid, in accordance with the following Table A. Amino acids comprising the peptides described herein will be understood to be in the L- or D-configuration. Amino acids described herein, may be modified by methylation, amidation, acetylation or substitution with other chemical groups which may change the circulating half-life of the peptide without adversely affecting their biological activity. Additionally, a disulfide linkage may be present or absent in the peptides of the invention. Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and non-standard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-amino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

It will be appreciated by a person of skill in the art the aspects of the individual amino acids in a peptide or polypeptide described herein may be substituted. Amino acid sequence identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, J Mol. Biol. 215: 403-410 and ALTSCHUL et al. (1997), Nucleic Acids Res. 25: 3389-3402.

Furthermore, it will be appreciated by a person of skill in the art that certain substitutions are more likely to result in retention of activity. For example, amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine.

Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Furthermore, the isolated polypeptide comprising SEQ ID NO:1 or a sequence comprising 20 amino acid having at least 90% identity to SEQ ID NO:1 may have 18 amino acids that are identical to those in SEQ ID NO:1. Furthermore, the isolated polypeptide comprising SEQ ID NO:2 or a sequence comprising 10 amino acid having at least 90% identity to SEQ ID NO:2 may have 9 amino acids that are identical to those in SEQ ID NO:2. Furthermore, the isolated polypeptide comprising SEQ ID NO:3 or a sequence comprising 15 amino acid having at least 90% identity to SEQ ID NO:3 may have 14 amino acids that are identical to those in SEQ ID NO:3.

Alternatively, the isolated polypeptides may have 55 amino acids, or the isolated polypeptides may have 54 amino acids, or the isolated polypeptides may have 53 amino acids, or the isolated polypeptides may have 52 amino acids, or the isolated polypeptides may have 51 amino acids, or the isolated polypeptides may have 50 amino acids, or the isolated polypeptides may have 49 amino acids, or the isolated polypeptides may have 48 amino acids, or the isolated polypeptides may have 47 amino acids, or the isolated polypeptides may have 46 amino acids, or the isolated polypeptides may have 45 amino acids, or the isolated polypeptides may have 44 amino acids, or the isolated polypeptides may have 43 amino acids, or the isolated polypeptides may have 42 amino acids, or the isolated polypeptides may have 41 amino acids, or the isolated polypeptides may have 40 amino acids, or the isolated polypeptides may have 39 amino acids, or the isolated polypeptides may have 38 amino acids, or the isolated polypeptides may have 37 amino acids, or the isolated polypeptides may have 36 amino acids, or the isolated polypeptides may have 35 amino acids, or the isolated polypeptides may have 34 amino acids, or the isolated polypeptides may have 33 amino acids, or the isolated polypeptides may have 32 amino acids, or the isolated polypeptides may have 31 amino acids, or the isolated polypeptides may have 30 amino acids, or the isolated polypeptides may have 29 amino acids, or the isolated polypeptides may have 28 amino acids, or the isolated polypeptides may have 27 amino acids, or the isolated polypeptides may have 26 amino acids, or the isolated polypeptides may have 25 amino acids, or the isolated polypeptides may have 24 amino acids, or the isolated polypeptides may have 23 amino acids, or the isolated polypeptides may have 22 amino acids, or the isolated polypeptides may have 21 amino acids, or the isolated polypeptides may have 20 amino acids, or the isolated polypeptides may have 19 amino acids, or the isolated polypeptides may have 18 amino acids, or the isolated polypeptides may have 17 amino acids, or the isolated polypeptides may have 16 amino acids, or the isolated polypeptides may have 15 amino acids, or the isolated polypeptides may have 14 amino acids, or the isolated polypeptides may have 13 amino acids, or the isolated polypeptides may have 12 amino acids, or the isolated polypeptides may have 11 amino acids, or the isolated polypeptides may have 10 amino acids, or the isolated polypeptides may have 9 amino acids, or the isolated polypeptides may have 8 amino acids, or the isolated polypeptides may have 7 amino acids, or the isolated polypeptides may have 6 amino acids, or the isolated polypeptides may have 5 amino acids. Alternatively, the isolated polypeptides may have between 10 and 50 amino acids, or the isolated polypeptides may have between 11 and 50 amino acids, or the isolated polypeptides may have between 12 and 50 amino acids, or the isolated polypeptides may have between 13 and 50 amino acids, or the isolated polypeptides may have between 14 and 50 amino acids, or the isolated polypeptides may have between 13 and 45 amino acids, or the isolated polypeptides may have between 13 and 40 amino acids, or the isolated polypeptides may have between 13 and 35 amino acids, or the isolated polypeptides may have between 13 and 30 amino acids, or the isolated polypeptides may have between 13 and 25 amino acids, or the isolated polypeptides may have between 13 and 20 amino acids, or the isolated polypeptides may have between 14 and 50 amino acids, or the isolated polypeptides may have between 14 and 35 amino acids, or the isolated polypeptides may have between 14 and 30 amino acids, or the isolated polypeptides may have between 14 and 29 amino acids, or the isolated polypeptides may have between 14 and 28 amino acids, or the isolated polypeptides may have between 14 and 27 amino acids, or the isolated polypeptides may have between 14 and 26 amino acids, or the isolated polypeptides may have between 14 and 25 amino acids, or the isolated polypeptides may have between 14 and 24 amino acids, or the isolated polypeptides may have between 14 and 23 amino acids, or the isolated polypeptides may have between 14 and 22 amino acids, or the isolated polypeptides may have between 14 and 21 amino acids, or the isolated polypeptides may have between 14 and 20 amino acids, or the isolated polypeptides may have between 14 and 19 amino acids, or the isolated polypeptides may have between 14 and 18 amino acids, or the isolated polypeptides may have between 14 and 17 amino acids, or the isolated polypeptides may have between 14 and 16 amino acids, or the isolated polypeptides may have between 14 and 15 amino acids.

Nomenclature used to describe the peptides or polypeptides may follow the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the name of the amino acid, in accordance TABLE A.

TABLE A

Nomenclature and abbreviations of the 20 standard L-amino acids commonly found in naturally occurring peptides

| Full name | Three-letter abbreviation | One-letter abbreviation |
| --- | --- | --- |
| Alanine | Ala | A |
| Cysteine | Cys | C |
| Aspartic acid | Asp | D |
| Glutamic acid | Glu | E |

TABLE A-continued

Nomenclature and abbreviations of the 20 standard L-amino acids commonly found in naturally occurring peptides

| Full name | Three-letter abbreviation | One-letter abbreviation |
| --- | --- | --- |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

Peptides may be modified in a variety of conventional ways well known to the skilled artisan. Examples of modifications include the following. The terminal amino group and/or carboxyl group of the peptide and/or amino acid side chains may be modified by alkylation, amidation, or acylation to provide esters, amides or substituted amino groups. Heteroatoms may be included in aliphatic modifying groups. This is done using conventional chemical synthetic methods. Other modifications include deamination of glutamyl and asparaginyl residues to the corresponding glutamyl and aspartyl residues, respectively; hydroxylation of proline and lysine; phosphorylation of hydroxyl groups of serine or threonine; and methylation of amino groups of lysine, arginine, and histidine side chains (see, for e.g.: T. E. Creighton, Proteins: Structure and Molecular Properties, W.H. Freeman & Co. San Francisco, Calif., 1983).

As used herein 'isolated', is meant to encompass a substance (such as, a polynucleotide or polypeptides or peptide) has been substantially separated or purified away from other components, such as biological components, with which it would otherwise be associated, for example in vivo, so that the isolated substance may be itself be manipulated or processed. The term 'isolated' therefore includes substances purified by purification methods known in the art, as well as substances prepared by recombinant expression in a host, as well as chemically synthesized substances. In some embodiments, a compound is 'isolated' when it is separated from the components that naturally accompany it so that it is at least 60%, more generally 75% or over 90%, by weight, of the total relevant material in a sample. Thus, for example, a polypeptides that is chemically synthesized or produced by recombinant technology may be generally substantially free from its naturally associated components. A polynucleotide may be substantially pure when it is not immediately contiguous with (i.e., covalently linked to) the coding sequences with which it is normally contiguous in the naturally occurring genome of the organism from which the DNA of the invention is derived. An isolated compound can be obtained, for example, by extraction from a natural source; by expression of a recombinant nucleic acid molecule encoding a polypeptides compound; or by chemical synthesis. Purity can be measured using any appropriate method such as column chromatography, gel electrophoresis or HPLC.

One or both, but usually one terminus of the peptide, may be substituted with a lipophilic group, usually aliphatic or aralkyl group, which may include heteroatoms. Chains may be saturated or unsaturated. Conveniently, commercially available aliphatic fatty acids, alcohols and amines may be used, such as caprylic acid, capric acid, lauric acid, myristic acid and myristyl alcohol, palmitic acid, palmitoleic acid, stearic acid and stearyl amine, oleic acid, linoleic acid, docosahexaenoic acid, etc. (see, for e.g.: U.S. Pat. No. 6,225,444). Preferred are unbranched, naturally occurring fatty acids between 14-22 carbon atoms in length. Other lipophilic molecules include glyceryl lipids and sterols, such as cholesterol. The lipophilic groups may be reacted with the appropriate functional group on the oligopeptide in accordance with conventional methods, frequently during the synthesis on a support, depending on the site of attachment of the oligopeptide to the support. Lipid attachment is useful where oligopeptides may be introduced into the lumen of the liposome, along with other therapeutic agents for administering the peptides and agents into a host.

Depending upon their intended use, particularly for administration to mammalian hosts, the subject peptides may also be modified by attachment to other compounds for the purposes of incorporation into carrier molecules, changing peptide bioavailability, extending or shortening half-life, controlling distribution to various tissues or the blood stream, diminishing or enhancing binding to blood components, and the like. The prior examples serve as examples and are non-limiting.

Peptides may be prepared in a number of ways. Chemical synthesis of peptides is well known in the art. Solid phase synthesis is commonly used and various commercial synthetic apparatuses are available, for example automated synthesizers by Applied Biosystems Inc., Foster City, Calif.; Beckman; etc. Solution phase synthetic methods may also be used, particularly for large-scale productions.

Peptides may also be present in the form of a salt, generally in a salt form which is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

The isolated polypeptides as described herein may inhibit an interaction between palmitoyl acyl transferase zinc-finger DHHC type containing 17 (zD17) and c-jun N-terminal kinase (JNK). The isolated polypeptides may further comprise a delivery and targeting moiety conjugated to the isolated polypeptides. Optionally, the delivery and targeting moiety may be selected from one or more of: ligands, protein transduction domains, or antibodies. Optionally, the protein transduction domain may be the cell-membrane transduction domain of the HIV-1 Tat protein. The HIV-1 Tat protein may form a fusion protein with the isolated polypeptides described herein (for example, SEQ ID NOs:1-3).

Delivery of bioactive molecules, such as the polypeptides or peptides described herein, to a cell or cells in a reasonably efficient manner may require more than just the "dumping" of the naked peptide on to the cell, or administering the naked peptide into the patient or test subject. Agents that enable delivery or targeting of bioactive molecules into cells in a suitable manner so as to provide an effective amount, such as a pharmacologically effective amount are known in the art, and are described in, for e.g.: Dietz et al. (2004). *Mol Cell. Neurosci* 27: 85-131. The peptides or polypeptides described herein may be conjugated to such a delivery and targeting (also referred to herein as "dat") moiety or moieties. The term delivery and targeting (dat) moiety as used herein is meant to encompass any moiety that assists in delivering and/or targeting the peptides or polypeptides described herein to a target cell or tissue or within a target cell or within the cells of a target tissue. Furthermore, a "dat moiety" may "assist" in delivery and/or targeting by virtue of promoting the biological efficacy of the peptides or polypeptides described herein.

Examples of "dat moieties" may include liposomes, lipid particles, antibodies, receptor ligands, protein transduction domains (PTD), and viral vectors that may be coupled to the PTEN inhibiting peptide or polypeptides as described herein. For example, where delivery to the brain is desired, isolated peptides or polypeptides described herein may be conjugated to antibodies that bind brain endothelial cell receptors resulting in endocytosis/transcytosis of the receptor and bound ligands (for example, U.S. Pat. No. 7,744,879). Peptides or polypeptides may be conjugated to a PDT, for example the HIV TAT protein (trans-activating transcriptional activator protein), which allows peptides to transverse cell membranes via endocytosis.

Examples of PTDs include, but are not limited to: *Antennapedia* homeodomain (Perez et al. (1992) *J. Cell Sci* 102: 717-722); transportan (Pooga et al. (1998) *FASEB J* 12: 67-77); the translocation domains of diphtheria toxin (Stenmark et al. (1991) *J Cell Biol* 113:1025-1032) and Wiedlocha et al. (1994) *Cell* 76: 1039-1051); and HIV-TAT (Demarchi et al. (1996) *J Virol.* 70: 4427-4437). Other examples and related details of such protein transduction domains are described in Dietz, supra and references cited therein. Furthermore, to reduce peptide degradation during whole body delivery, peptides may be conjugated to small micelles or liposomes using modified PEG, or subject to end-modifications, such as C-terminal amidation or N-terminal acetylation.

A ligand may function as a delivery and targeting moiety by selectively binding or having a specific affinity for another substance. A ligand may be recognized and bound by a specific binding body or binding partner, or receptor. Examples of ligands suitable for targeting may be selected from antigens, haptens, biotin, biotin derivatives, lectins, galactosamine and fucosylamine moieties, receptors, substrates, coenzymes and cofactors among others.

Another type of delivery and targeting moiety is an antibody, which is defined to include all classes of antibodies, including, without limitation: monoclonal antibodies, chimeric antibodies, Fab fractions, fragments and derivatives thereof. Other delivery and targeting moieties may include enzymes, especially cell surface enzymes such as neuraminidases, plasma proteins, avidins, streptavidins, chalones, cavitands, thyroglobulin, intrinsic factor, globulins, chelators, surfactants, organometallic substances, staphylococcal protein A, protein G, cytochromes, lectins, certain resins, and organic polymers.

Delivery and targeting moieties may also include various substances such as any proteins, protein fragments or polypeptides with affinity for the surface of any cells or tissues to be targeted by the peptide or polypeptides described herein. These proteins may be produced through recombinant DNA, genetic and molecular engineering techniques know in the art. For example, SEQ ID NOs:4-9 show the isolated polypeptides of SEQ ID NOs:1-3 conjugated to the HIV TAT protein. Of particular use would be any suitable membrane transfer proteins to facilitate the transfer of the peptide or polypeptides described herein to the target cell interior (for example, a PTD as described herein).

In therapeutic applications, the compositions described herein may be administered to a subject suffering from one or more symptoms of a disease associated with excitotoxic stress in an amount sufficient to cure or at least partially prevent or arrest the disease and/or its complications or to help alleviate the symptoms associated therewith. An amount adequate to accomplish this is defined as a "therapeutically effective dose" or "a therapeutically effective amount". Amounts effective for this use will depend upon the severity of the disease and the general state of the subject's health. Single or multiple administrations of the compositions may be administered depending on the dosage and frequency as required and tolerated by the patient. A composition generally would provide a sufficient quantity of the active peptide or polypeptides described herein to effectively treat (for example, to at least ameliorate one or more symptoms) in the subject.

The concentration of peptide or polypeptides described herein can vary widely, and may be selected primarily based on fluid volumes, viscosities, body weight and the like in accordance with the particular mode of administration selected and the subject's needs. Concentrations, however, will typically be selected to provide dosages ranging from about 0.1 or 1 mg/kg/day to about 50 mg/kg/day and sometimes higher. Typical dosages range from about 3 mg/kg/day to about 3.5 mg/kg/day, preferably from about 3.5 mg/kg/day to about 7.2 mg/kg/day, more preferably from about 7.2 mg/kg/day to about 11.0 mg/kg/day, and most preferably from about 11.0 mg/kg/day to about 15.0 mg/kg/day. In certain preferred embodiments, dosages range from about 10 mg/kg/day to about 50 mg/kg/day. In certain embodiments, dosages may range from about 20 mg to about 50 mg given orally twice daily. It will be appreciated that such dosages may be varied to optimize a therapeutic regimen in a particular subject or group of subjects.

In certain embodiments, the peptide or polypeptides described herein may be administered orally (e.g., via a tablet) or as an injectable in accordance with standard methods well known to those of skill in the art. In other embodiments, peptide or polypeptides described herein, may also be delivered through the skin using conventional transdermal drug delivery systems, i.e., transdermal "patches" wherein the active agent(s) are typically contained within a laminated structure that serves as a peptide or polypeptides delivery device to be affixed to the skin. In such a structure, the composition is typically contained in a layer, or "reservoir", underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

The peptide or polypeptides described herein may be administered orally. Peptide or polypeptides delivery may be enhanced by the use of protective excipients. This is typically accomplished either by complexing the polypeptides with a composition to render it resistant to acidic and enzymatic hydrolysis or by packaging the polypeptides in an appropriately resistant carrier such as a liposome. Means of protecting polypeptides for oral delivery are well known in the art.

Additional pharmacologically active agents may be delivered along with the primary active agents, e.g., the peptides or polypeptides described herein. The peptide or polypeptides may be co-administered with another pharmaceutically active agent to enhance the therapeutic effect on the target cell or tissue by delivering a second compound with a similar or complimentary activity. In one embodiment, such agents include, but are not limited to agents that reduce the risk of a stroke or ischemic injury and/or complications thereof. Such agents include, but are not limited to Anticoagulants (for example, Acenocoumarol, Coumatetralyl, Dicoumarol, Ethyl biscoumacetate, Phenprocoumon, Warfarin, Clorindione, Diphenadione, Phenindione, Tioclomarol, Bemiparin, Certoparin, Dalteparin, Enoxaparin, Nadroparin, Parnaparin, Reviparin, Tinzaparin, Fondaparinux, Idraparinux, Danaparoid, Sulodexide, Dermatan sulfate, Apixaban, Betrixaban, Edoxaban, Otamixaban, Rivaroxaban, Hirudin, Bivalirudin, Lepirudin, Desirudin, Argatroban, Dabigatran, Melagatran, Ximelagatran, REG1, Defibrotide, Ramatroban, Antithrombin III, and Drotrecogin alfa), Antiplatelet drugs (for example, Abciximab, Eptifibatide, Tirofiban, Clopidogrel, Prasugrel, Ticlopidine, Ticagrelor, Beraprost, Prostacyclin, Iloprost, Treprostinil, Acetylsalicylic acid/Aspirin, Aloxiprin, Carbasalate calcium, Indobufen, Triflusal, Dipyridamole, Picotamide, Terutroban, Cilostazol, Dipyridamole, Triflusal, Cloricromen, Ditazole), and Thrombolytic and Firbrinolytic drugs (for example, tissue plasminogen activator (tPA) or recombinant tissue plasminogen activator (rtPA) such as Alteplase, Reteplase, Tenecteplase, Urokinase, Saruplase, Streptokinase, Anistreplase, Monteplase, Ancrod, Fibrinolysin, and Brinase), and the like or in combination with other neuroprotective agents.

Depending upon their intended use, particularly for administration to mammalian hosts, the subject peptides may also be modified by attachment to other compounds for the purposes of incorporation into carrier molecules, changing peptide bioavailability, extending or shortening half-life, controlling distribution to various tissues or the blood stream, diminishing or enhancing binding to blood components, and the like. The prior examples serve as examples and are expressly non-limiting.

An isolated polynucleotide may comprise a nucleotide sequence encoding an isolated polypeptides as described herein. The compositions described herein may include a polypeptide as described herein and a carrier. Optionally, the carrier may be a pharmaceutically acceptable carrier.

A vector may include an isolated polynucleotide as described herein. A cell may include a vector described herein. Furthermore, a cell comprising the polynucleotide described herein, may have the polynucleotide operably linked to an expression control sequence.

Methods of protecting a cell from excitotoxic stress are described herein. The methods may involve delivering an isolated polypeptide as described herein to a cell. Such delivery may protect a cell from cytotoxic stress. The cytotoxic stress may be excitotoxic stress. A method may involve: (a) delivering the vector described herein to the cell; and (b) expressing the polynucleotide carried by the vector. A method may involve: (a) delivering the vector described herein to a cell; and (b) maintaining the cell under conditions permitting expression of the polynucleotide carried by the vector. Optionally, the methods may involve delivering a vector to a cell in an in vivo setting. Optionally, a method may involve delivering the vector to the cell in an ex vivo setting. Optionally, a method may involve delivering the vector to the cell in an in vitro setting.

'Cytotoxic stress' as used herein is meant to encompass a broad range of cellular stresses including pathologic changes in response to excessive levels of cytotoxic oxidants and free radicals in a cells environment (for example, oxidative stress), may be immune mediated, may also include excitotoxic stresses.

'Excitotoxic stress' as used herein is an important component of disorders such as stroke and other neurodegenerative diseases. There is evidence that the toxic effects of excitotoxic stress may be exerted through mechanisms that result in both acute and delayed forms of cell death, when receptors for the excitatory neurotransmitter glutamate (glutamate receptors) such as the NMDA receptor and AMPA receptor are overactivated. Excitotoxins like NMDA and kainic acid which bind to these receptors, as well as pathologically high levels of glutamate, can cause excitotoxicity by allowing high levels of calcium ions (Ca2+) to enter the cell. Ca2+ influx into cells can activate a number of enzymes, including phospholipases, endonucleases, and proteases such as calpain. These enzymes are capable of damaging cell structures like the cytoskeleton, cell membranes, and DNA. Excitotoxicity may be involved in spinal cord injury, stroke, traumatic brain injury, alcoholism or alcohol withdrawal, and neurodegenerative diseases of the central nervous system (CNS) such as multiple sclerosis, Alzheimer's disease, amyotrophic lateral sclerosis (ALS), Parkinson's disease, and Huntington's disease.

As provided herein, a method of treating a disease associated with cytoxicity or excitotoxicity may involve: administering a biologically effective amount of the polypeptides described herein or the pharmaceutical compositions described herein to a subject in need thereof. The biologically effective amount may be an amount sufficient to prevent cytoxicity/excitotoxicity-induced cell death. The disease associated with excitotoxicity may be selected from the following without limitation: spinal cord injury, stroke, traumatic brain injury, alcoholism or alcohol withdrawal, and neurodegenerative diseases of the central nervous system (CNS) such as multiple sclerosis, Alzheimer's disease, amyotrophic lateral sclerosis (ALS), Parkinson's disease, and Huntington's disease. Optionally, the disease associated with cytoxicity/excitotoxicity is stroke.

Experimental and Methodology
Cell Cultures and Materials

All animal experiments were approved by the Animal Care Committee of the University of British Columbia. Primary cortical cultures were prepared from Wistar rat (UBC Animal Care Centre, Vancouver, BC, Canada) brains at embryonic days 18-19. Cultures were maintained in Neurobasal medium supplemented with B27 and 0.5 mM glutamax (Invitrogen™) as described previously (Yang et al., 2009).

For biochemical studies, neurons were seeded in six-well culture plates with a density of $7.5 \times 10^5$ cells per well. For LDH assay and cell death detection, 24-well culture plates were used with a neuron density of $2.5 \times 10^5$ cells per well. Neurons of 14-17 days in vitro (DIV) were used for experiments. For immunostaining, rat hippocampal neurons were seeded on glass coverslips in twelve-well plates with a density of $1.25 \times 10^5$ cells per well. HEK 293 cells were maintained in DMEM (Invitrogen™) supplemented with 10% fetal bovine serum and 1% penicillin/streptomycin. For protein expression in cell lines, cells were transfected with Calcium Phosphate Transfection reagent (Promega™, San Luis Obispo, Calif., USA) and used 24 h later as described previously (Yang et al., 2009). The JNK inhibitor, L-JNKI, was purchased from Alexis Biochemicals™ (San Diego, Calif.). Thrombin was obtained from BIOPUR™ (Bubendorf, Switzerland). Other assay reagents without indication were obtained from Sigma™.

Plasmids and Antibodies

The GST-tagged full-length and fragments of zD17 constructs were created by cloning zD17 and fragment cDNA sequences into a pGEX-4T-1 vector with a myc epitope sequence at the N-terminus. The GST-JNK3 construct was cloned into the same vector. Myc-tagged fragments of zD17 were also cloned into pcDNA3 to generate expression constructs. GFP-JNK1 and GFP-JNK2 expression constructs were created by cloning cDNA sequences into pEGFP-C1 plasmids. The vectors encoding myc-zD13, myc-zD17, GFP-PSD95, GFP-PSD95$^{C3,5S}$, GFP-SNAP25 and HA-SYTI were generously provided by Dr. Alaa Husseini's lab. The GFP-JNK3 construct was a gift from Dr. Vsevolod V. Gurevich (Song et al. 2006). The constructs expressing FLAG-JNK3; FLAG-MKK3, FLAG-MKK4, FLAG-MKK6, FLAG-MKK7 wt, and FLAG-kiMKK7 were purchased from Addgene™.

The primary antibodies used to detect JNK1, activated-caspase3 and FLAG (DDDDK) epitopes were obtained from Abcam™ (Cambridge, Mass.). Anti-zD17, anti-synaptophysin and anti-GFP were purchased from Sigma™. Anti-GST and anti-Tau1 were purchased from Abm (Richmond, BC, Canada) and Millipore™, respectively. The antibody against PSD-95 was obtained from Synaptic System™ (Goettingen, Germany). Purified IgG was supplied by Jackson ImmunoResearch™. All other primary antibodies were purchased from Cell Signaling Technology (Danvers, Mass.). Secondary antibodies were HRP-conjugated anti-mouse (Cell Signaling Technology™), anti-rabbit (Perkin Elmer™), anti-GFP (Santa Cruz Biotechnology™), and anti-myc (Invitrogen™) Fluorescent Alexa 488- and Alexa 568-conjugated anti-mouse IgG1, IgG2a and anti-rabbit IgG were obtained from Invitrogen™.

Protein Extraction and Immunoblotting

The protocols for protein extraction have been described previously (Yang et al., 2009). For co-immunoprecipitation, cultured cells were washed with ice-cold PBS followed by incubation with 0.5 ml Gentle Lysis Buffer (GLB) containing 25 mM Tris-HCl (pH 7.4), 2 mM EDTA, 1 mM EGTA, 10 mM NaCl, 0.5% Triton X-100 and 10% Glycerol supplemented with the Complete Protease Inhibitor Tablets (Roche Applied Science™, Indianapolis, Ind., USA) and 1 mM PMSF. Total protein concentration was determined with the BioRad™ Protein Assay kit. Lysates were first precleaned by incubating with Protein A-Sepharose beads (Roche Applied Science™) for 1 h at 4° C., followed by incubation with indicated antibodies (>16 h at 4° C.) and protein A Sepharose bead (2 h at 4° C.). Lysates of rat brain tissues were precleaned with IgG and protein A-beads. Immunoprecipitates were washed three times with GLB buffer; boiled in 2× loading buffer with 1 mM dithiothreitol (DTT) for 3 min; and analyzed with SDS-PAGE as described previously (Yang et al., 2009). The relative intensities of the bands on immunoblots were analyzed and quantified using Image J™ (NIH).

Kinase Assays

JNK activity was measured with an in vitro kinase assay as described elsewhere (see, for e.g.: Khatlani et al., 2007). Briefly, cell lysates were prepared and JNK was immunoprecipitated with specific antibodies. The immnoprecipitates were then resuspended in 1× kinase buffer (Cell Signaling Technology™) supplemented with 200 µM ATP and 250 µg/ml GST-c-jun (1-89), and incubated at 30° C. for 30 min. Reactions were terminated by the addition of SDS-PAGE sample buffer. Phosphorylated c-jun was resolved by SDS-PAGE and detected with anti-p-c-jun.

Affinity Binding Assay and Peptide Array

An affinity binding assay was used to assess direct interaction between JNK3 and zD17. GST-fused full-length zD17 (GST-zD17$^{1-632}$), zD17 fragments (GST-zD17$^{1-310}$, GST-zD17$^{405-479}$, GST-D17$^{550-632}$, GST-zD17$^{125-140}$, GST-zD17$^{140-190}$ GST-zD17$^{190-210}$) and JNK3 (GST-JNK3) were purified from *E. coli* BL21 with Glutathione Sepharose 4B (GE Healthcare™). Purified GST fusion proteins were resolved on SDS-PAGE and transferred onto nitrocellulose membranes. To prepare bait proteins, purified GST-myc-zD17 and GST-JNK3 were digested with thrombin overnight at room temperature, followed by clearance with β-Aminobenzamidine-agarose (Sigma™) for 1 h at 4° C. The bait proteins were then prepared in affinity binding buffer (TBST with 5% skim-milk and 4% sucrose) at a concentration of 10 μg/ml. After blocked with affinity binding buffer at room temperature for 4 h, the membrane was incubated with bait proteins overnight at 4° C., and washed three times with TBST. Bound bait proteins were detected with primary antibody against myc-epitope or JNK3, and HRP-conjugated secondary antibody. For mapping detailed interaction motifs, a peptide spot array was synthesized by PepMetric Technologies™ (Vancouver, Canada). The assay contained overlapping peptides (15-mer peptides with five amino acids shift) to cover the N-terminal cytosolic domain of zD17 (zD17$^{1-325}$). The array membrane was initialized by washing twice with methanol for 10 min at room temperature, followed by three washes with TBST. The conditions for the preparation of array membrane, incubation with purified JNK3, and detection of bound bait protein, were the same as those of the affinity binding assays.

LDH Assay and Cell Death Detection

Neuronal cultures were challenged with indicated concentrations of NMDA for 1 h, followed by 24 h survival. The release of lactate dehydrogenase (LDH) was measured with an in vitro toxicology assay kit (Sigma™) according to the manufacturer's instructions. Spectrophotometric measurement was performed on a Multilabel Plate Reader (Envision™ 2103, Perkin Elmer™). The LDH reading represents the primary absorbance at a wavelength of 490 nm after subtraction of background absorbance at 690 nm. LDH readings were then converted to a percentage of neuronal death by dividing by the readings from cultures incubated with 1% triton for 15 min representing total LDH. Following the LDH assay, propidium iodide (PI) (Sigma™) was added to the medium at a final concentration of 1 μg/ml and neurons were stained for 30 min at 30° C. After fixation with 4% paraformaldehyde, neurons were washed with 1×PBS and stained with Hoechst™ 33342 (Sigma™). The fluorescence of PI and Hoechst™ were examined with laser microscopy and analyzed with ImageJ™.

Mitochondria Fractionation

Cultured neurons were lysed on ice for 10 min in TEEN-SKM buffer containing 20 mM Tris-HCl (pH7.5), 10 mM KCl, 1.5 mM MgCl$_2$, 1 mM EGTA, 1 mM EDTA, 1 mM DTT supplemented with the Complete Protease Inhibitor tablets. The lysates were homogenized with a 28$^{1/2}$G syringe for a total of 8 times on ice, followed by centrifugation twice at 700 g for 10 min at 4° C. The supernatant was then centrifuged at 10,000 g for 30 min at 4° C. to enrich mitochondria in the pellet. The cytosolic fraction was collected from the supernatant after further centrifugation at 100,000 g for 1 h at 4° C. 1× and 4×LB were added to the mitochondrial and cytosolic fractions, respectively. Equivalent amounts of samples were resolved by SDS-PAGE and blotted with antibodies against Cytochrome c and Bax.

Immunostaining and Laser Microscopy

Cultured hippocampal neurons on glass coverslips were used for immunostaining. After treatments indicated in the text, neurons were fixed with 2% paraformaldehyde for 3 min at room temperature followed by permeabilization with ice-cold methanol for 10 min at −20° C. The coverslips were then washed three times with PBS and immunostained with appropriate antibodies dissolved in PBS for 1 h at room temperature. After washing three times with PBS, coverslips were incubated with Alexa-labeled secondary antibodies from Invitrogen for an additional 1 h. For mitochondrial detection, neuronal cultures were incubated at 37° C. for 30 min with 2 μM MitoTracker-TR (Invitrogen™). Coverslips were then fixed and mounted with ProLong Gold Antifade Reagent (Invitrogen™). Fluorescence was captured using a Zeiss Observer Z1™ microscope and all images were analyzed with ImageJ™ and processed using Adobe Photoshop™.

Transient Ischemia in Rats

Adult male Sprague-Dawley (SD) rats weighing 250-290 g were employed for transient middle cerebral artery occlusion. Rats were anaesthetized with 5% isofluorane and maintained with 2% isofluorane in 70% N$_2$O and 30% O$_2$ using a face mask. 5 mg/kg ketoprofen was given pre-surgery to block pain. Rectal temperature was maintained at 37° C. during surgery with a homeothermic blanket system (Harvard Apparatus™, Holliston, Mass.). The scalp was incised at the midline and the skull was exposed. The skull was thinned with a dental drill at a region ipsilateral to the expected ischemia zone (2 mm posterior and 5 mm lateral from the bregma). A laser probe of the Doppler flowmeter (Perimed™, Jäffälla, Sweden) was placed at this location during surgery to detect cerebral blood flow (CBF) (Nagal et al., 2010). Transient MCAo was induced using a method of intraluminal vascular occlusion described elsewhere (Aarts et al., 2002; Belayev et al., 1996; and Longa et al., 1989). Briefly, a poly-L-lysine coated 3-0 monofilament nylon suture (Harvard Apparatus™, Holliston, Mass.) with a rounded tip was advanced from the left common carotid artery into the internal carotid artery until a sudden drop of CBF was noted, indicating the blockade of the origin of the MCA. The success of induction of ischemia was confirmed by a fall of CBF to less than 25% of baseline level and by neurological assessment scores during MCAo (1 h after the onset). Two hours after MCAo, rats were re-anaesthetized and the suture was removed to allow reperfusion, confirmed by the increase of CBF at the same area.

Peptide Administration

Peptides were synthesized by PepMetric Technologies™ or GL Biochem™ (Shanghai, China). Peptides were prepared freshly in saline on the day of experiment at a stock concentration of 1 mg/ml. 1 mg/kg peptides were administrated at indicated times (30 min before, 2 h after or 6 h after the onset of ischemia) by a single intravenous injection at rat tails. NIMoEscr or NIMoEsh were injected at 4 h after MCAo onset to randomly chosen rats. For long-term studies, peptides were given 2 h after MCAo onset. Injections of NIMoEscr and NIMoEsh were made, brain damage was assessed and functional evaluations performed in a double-blind manner To examine the delivery of the peptide into the brain, 5 mg/kg FITC-labelled NIMoE or only saline was intravenously injected 1 h before perfusion. The rats were then perfused with PBS followed by fixation solution (4% paraformaldehyde in PBS). Brains were removed, postfixed in fixation solution for 2 h and then soaked in 20% sucrose-PBS buffer at 4° C. for 24 h. After rapid freezing in Tissue-Tek™ embedding medium (Sakura™, Torrance, Calif.) on dry ice, 20 μm sections were cut on a cryostat (Leica™ CM3050, Ontario, Canada) and examined for FITC fluorescence by a laser microscopy (Zeiss™, Axiovert 200).

Histological Assessment

Rats were allowed to survive for 24 h. After decapitation, the brains were immediately removed and serially sectioned in the coronal plane at a thickness of 2 mm with a slicer matrix (Zivic™, Pittsburgh, Pa.). A total of 8 sections were collected and then incubated in PBS with 1% 2,3,7-triphenyltetrazolium chloride at 37° C. for 10 min. The stained slices were then fixed in 4% paraformaldehyde and digitised with a colour flatbed scanner (MFC-8860DN, Brothers™). The infarct area within each section was traced and quantified using ImageJ™. The infarct volume was calculated using the formula: $V=d(A1+A2+ \ldots +A8)$ where V is the infarct volume ($mm^3$), d is the distance between sections, and A is the infarct area within each section.

Functional Tests

All animals were tested for neurological function during (1 h after onset) and 24 h after MCAo. Motor, sensory and coordination capacities were evaluated with modified Neurological Severity Scores (NSS) (Watanabe et al., 2004; Bederson et al., 1986). The motor system tested included 7 components including motor initiation test, free activity, posture, walking, tail suspension, hindlimb flexion and pushing test. Somatosensory tests included a tactile test and forelimb placing test. Coordination functions were assessed with 3 tests including a foot fault test, edge test and balance beam. Performance in the tests was evaluated on a cumulative scale from 0 to 2 (10 tests), except for two tests (tail suspension and balance beam in which scores ranged from 0 to Sand 0 to 4, respectively). The scores from each test were summed and represented as a single overall neurological score (0 to 27). The adhesive-removal test (Bouet et al., 2009) was used for further evaluation of somatosensory deficits. One piece of adhesive tape was wrapped around the right forepaw. The time spent on removing the tape from paw within 2 min was recorded.

Statistics

All values in text and figures are presented as mean±standard error of the mean. Student t-test or one-way ANOVA was performed using Excel software (Microsoft™). The limit of statistical significance was set at a P value <0.05.

EXAMPLES

Example 1

JNK Activation is Regulated by the zD17-MKK7-JNK Signaling Module

To examine the impact of palmitoyl acyl transferases (PATs) on JNK activation, several neuronal PATs were expressed individually with JNK3 in HEK293 cells. Under both resting and osmotic stress conditions (i.e. 400 mM sorbitol for 30 min.), zD17 increased JNK3 phosphorylation while other tested PATs showed no effects (data not shown). The kinase activity of JNK3 was also found to be enhanced by expression of zD17 (data not shown). The involvement of zD17's PAT activity was further examined by employing a PAT activity deficient mutant of zD17 (zD17Δ) (Huang et al., 2004). Similar to wildtype zD17, zD17Δ showed strong enhancement of JNK3 phosphorylation (data not shown). These results indicate that zD17 is selectively involved in activating JNK in a PAT activity-independent manner. Since zD17 does not have a canonical kinase domain, it was postulated whether zD17 might interact directly with JNK and modulate its activity. Using co-immunoprecipitation, it was found that JNK3 associated with zD17 in HEK293 cells, but not with other similar PATs (zD15 and zD20) (data not shown). GFP-JNK3 was found in the zD17 immunoprecipitates enriched by anti-myc antibody, but was not detected in zD15 or zD20 immunoprecipitates. The association of JNK3 was independent of zD17's PAT activity, as both zD17 wildtype and zD17Δ immunoprecipitated JNK3 (data not shown). Similar to JNK3, JNK1 and JNK2 were found to interact with zD17 when expressed in HEK293 cells (data not shown). In vitro, purified JNK3 was capable of binding purified myc-zD17 (data not shown). Thus, it was concluded that zD17 is a binding partner of JNK.

Since zD17 promoted JNK phosphorylation and activity, the role of several mitogen-activated protein kinase kinases (MAPKKs—i.e. MKK3, MKK4, MKK6, and MKK7), upstream activators of JNK, were examined in a potential signaling module (Weston and Davis, 2007). When MAPKKs were expressed in HEK293 cells, zD17 was able to co-immunoprecipitate the JNK activator MKK7. In contrast, the JNK activator MKK4, and the p38 activators MKK3 and MKK6, did not associate with zD17 (data not shown). To further confirm the functional involvement of MKK7, a kinase-inactive MKK7 (MKK7ki) was compared to MKK7 wt (Merritt et al., 1999). Since MKK7ki interacted with zD17 similar to MKK7 wildtype, MKK7ki was expressed as a dominant negative, resulting in attenuated JNK3 phosphorylation (data not shown). Moreover, the association of JNK3 and MKK7, assessed by co-immunoprecipitation, was strongly enhanced in the presence of zD17 (2.41±0.17 fold, $P<0.01$) (data not shown). These results suggest that zD17 recruits MKK7 and JNK to form a signaling module for JNK activation.

Example 2

Neuronal Excitotoxicity Promotes Formation of the zD17-JNK Module

Figure 2:
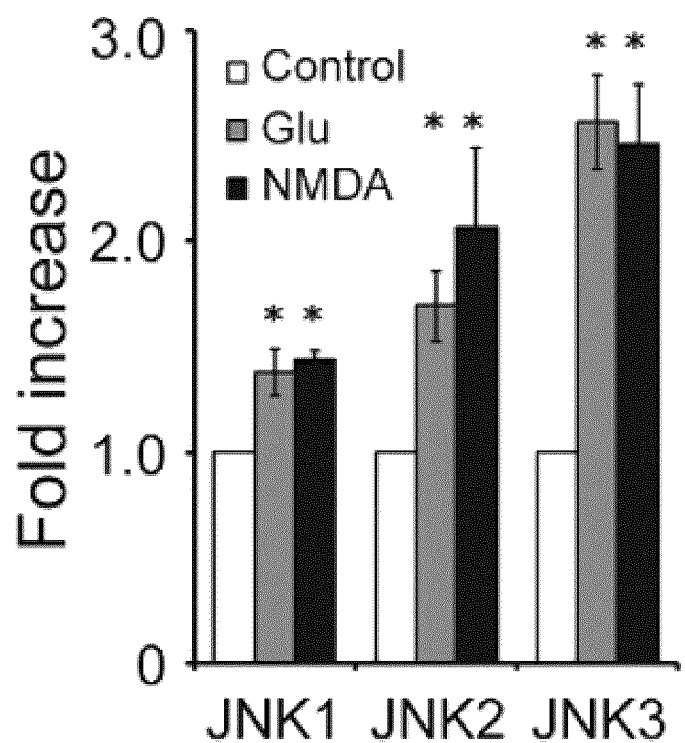
FIG. 2 shows a bar graph of glutamate and NMDA enhancing the zD17 interaction with JNK isoform 2 and 3, wherein the enhancement of JNK2 (Fold increase compared with control; Glutamate, 1.7±0.2; NMDA, 2.1±0.4) and on JNK3 (Glutamate, 2.6±0.2; NMDA, 2.5±0.3) are higher than that on JNK1 (Glutamate, 1.4±0.1; NMDA, 1.4±0.1).

As an important transducer of stress signals in the neuron, JNK is activated in response to various stresses such as excitotoxicity and inflammation (Borsello and Forloni, 2007). Accordingly, we asked whether the zD17-JNK signaling module is recruited in these scenarios. Inflammation induced by the cytokines, tumor necrosis factor-α (TNF-α) or interleukin-1β (IL-1β), as well as excitotoxicity induced by glutamate or N-methyl-D-aspartic acid (NMDA) stimulation robustly promoted the zD17-JNK3 interaction in cortical neuronal cultures (FIG. 1 (data not shown for NMDA)). Moreover, in comparison with stress-responsive isoforms JNK2 and JNK3, the JNK1-zD17 interaction was less sensitive to either NMDA or glutamate treatment (FIG. 2). Since excitotoxicity-induced JNK activation is predominantly mediated by MKK7 (Centeno et al., 2007), we focused on excitotoxicity as our cellular model to study mechanisms underlying activation of the zD17-JNK signaling module and its contribution to neuronal cell death.

Next the activation pathways by which the zD17-JNK signaling module is regulated by excitotoxicity were examined. ZD17 has been shown to interact with many different substrates, and it may be that changes in the interaction of zD17 with one or more of its substrates affects its availability for interaction with JNK3 (Huang et al., 2009). One substrate of zD17, postsynaptic density-95 (PSD-95) is especially relevant, because excitotoxicity has been shown to alter its palmitoylation and protein-interaction profile (Kornau et al., 1995; El-Husseini Ad et al., 2002; Kang et al., 2008). In HEK293 cells, overexpression of PSD-95 was shown to imped the zD17-JNK3 interaction and JNK3 phosphorylation (data not shown). Binding to PSD-95 showed interference with the zD17-JNK3 interaction (fold change; PSD-95, 0.82±0.03; P<0.01; PSD-95C3,5S, 1.25±0.07; P<0.05), and reduced JNK3 phosphorylation (fold change; PSD-95, 0.64±0.11; P<0.05; PSD-95C3,5S, 1.19±0.21; P=0.42) in HEK293 cells. This impact of PSD-95 was completely abolished by mutating its palmitoylation sites, which eliminated the interaction with zD17 (Huang et al., 2009). A broad spectrum palmitoylation inhibitor 2-bromopalmitate (2-BrPA) was used to inhibit the zD17 interaction with its substrates in cultured neurons (Huang et al., 2009; Yang et al., 2009). This treatment robustly enhanced the zD17-JNK3 interaction (data not shown). Excitotoxicity has been shown to mobilize PSD-95 to NMDA receptors (NMDAR), which initiates neurotoxic signaling (Kornau et al., 1995; Aarts et al., 2002). A previously described peptide, NR2B9c, was applied to block the PSD-95-NMDAR association (Aarts et al., 2002). This peptide, but not its mutated control NR2Baa, also impeded the enhancement of the zD17-JNK3 interaction (data not shown). Taken together, these results suggest that the PSD-95 contributes, at least partially, to the regulation of the zD17-JNK interaction in response to excitotoxicity.

Example 3

Identification of JNK Binding Motifs on zD17

Figure 3:
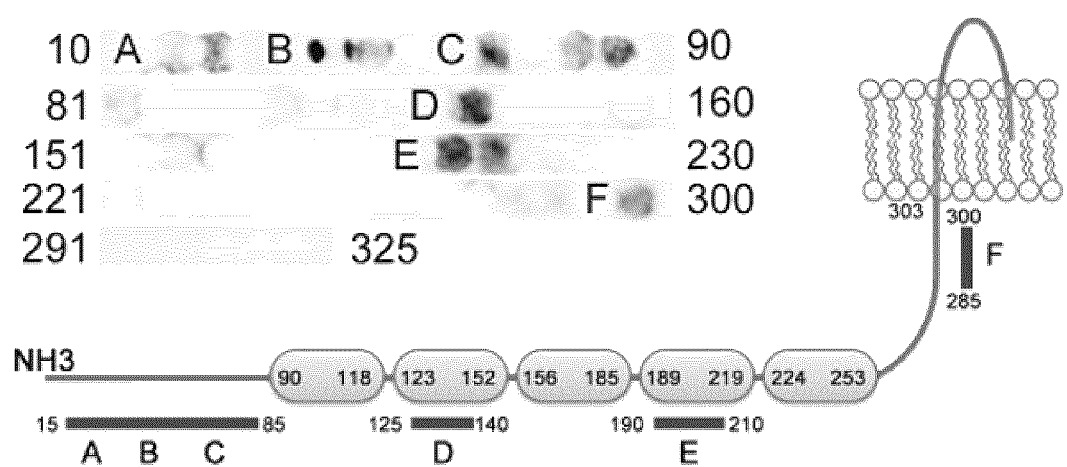
FIG. 3 shows an in vitro peptide scan of potential JNK-interacting motifs on zD17 N-terminal cytosolic domain, with interaction-positive regions plotted on the diagram showing the N-terminal part of zD17 and bold black lines with marks (A-F) indicate the potential JNK-interacting motifs from the peptide scan and their locations on zD17 are labelled beside the lines. Also, the ankyrin domains for protein interaction were plotted as rounded rectangles with locations indicated.
Figure 4:
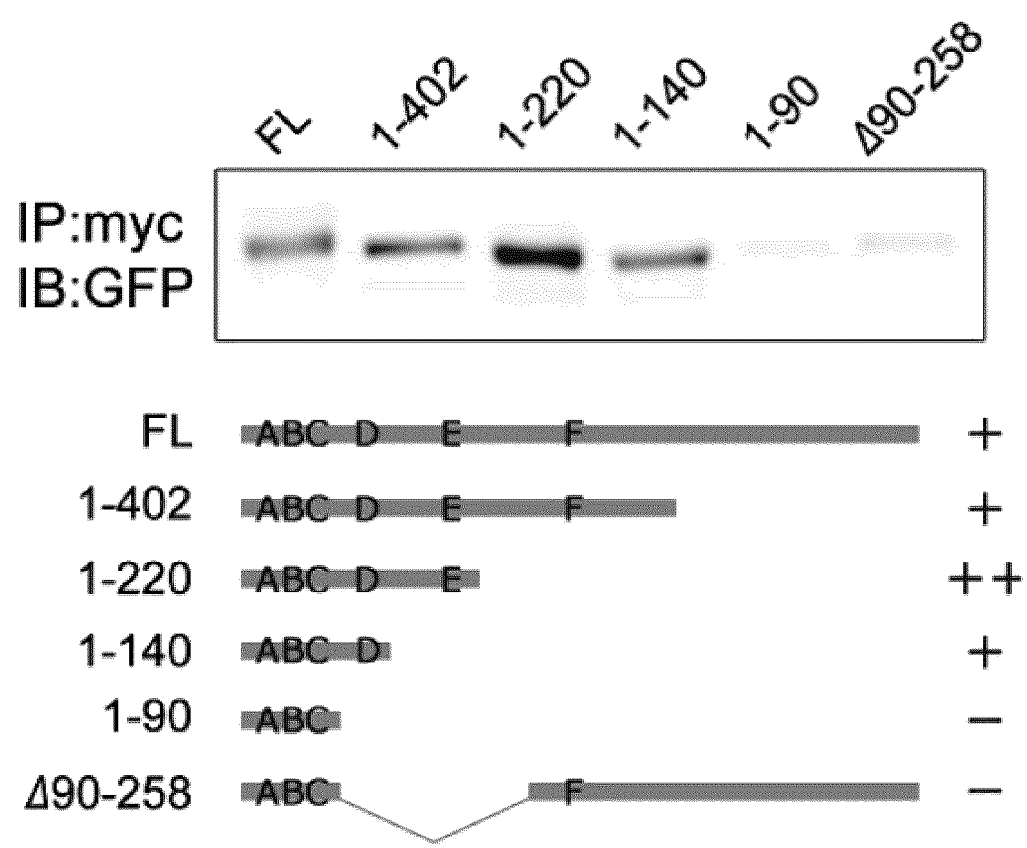
FIG. 4 shows two motifs located in different ankyrin domains, which are important for the zD17-JNK interaction. Myc-tagged full-length zD17 (FL) and fragments of zD17 with assorted deletions are indicated at bottom, and embedded potential interaction motifs (A-F) are labelled. The interaction ability (plus or minus) of these constructs is plotted.
Figure 5:
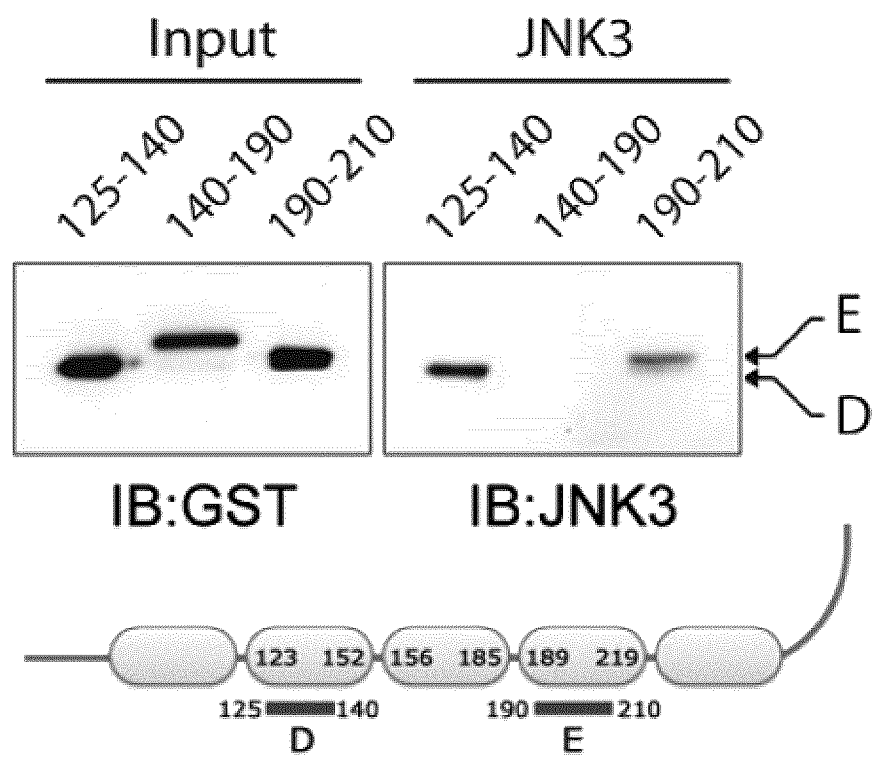
FIG. 5 shows that JNK3 binds to motif-D and motif-E on zD17. Motif-D, motif-E and the third ankyrin repeat in between, were fused with GST and purified. After incubation with JNK3, only motif-D and motif-E bound to JNK3.

To develop blockers of the zD17-JNK interaction, two novel JNK binding motifs were identified on zD17. JNK-interacting motifs are embedded at the N-terminus of zD17. Purified GST-tagged zD17 fragments are the cytosolic domains (CD1, zD171-310; CD2, zD17405-479; CD3, zD17550-632). Three cytosolic domains were purified (CD1, 2 and 3) of zD17 with a GST tag, and found that, in vitro, JNK3 binding predominantly occurred at CD1 (data not shown). To obtain further information, a peptide array containing 15mers with a 5aa shift was used to cover CD1 and identified regions on the membrane to which JNK3 bound (FIG. 3). Six potential binding regions in three categories were detected: N-terminus (motifs-A, -B, -C), ankyrin repeats (motifs-D, -E), and submembrane (motif-F). These zones were candidate regions and may not reflect actual binding domains. Thus, a series of zD17 deletion mutants were generated and examined their capability of interacting with JNK3 by co-immunoprecipitation (FIG. 4). Deleting CD2 and CD3 did not affect the zD17-JNK3 interaction. Deletion of motif-F did not reduce, but instead increased, the co-immunoprecipitation of JNK3. Removing motif-E diminished the interaction. Strikingly, further deleting motif-D, or selectively removing motifs-D and -E from full-length zD17 completely eliminated the interaction (FIG. 4C), suggesting the involvement of these two motifs in binding JNK3. Motifs-D and -E are located within the second and the fourth ankyrin repeats, respectively. Although zD17 contains five ankyrin repeats, our data indicate that JNK3 binds specifically to motifs-D and -E of zD17 with a preference for motif-D (FIG. 5).

Example 4

Isoform-Selective and Scenario-Selective Inhibition of JNK

Figure 6:
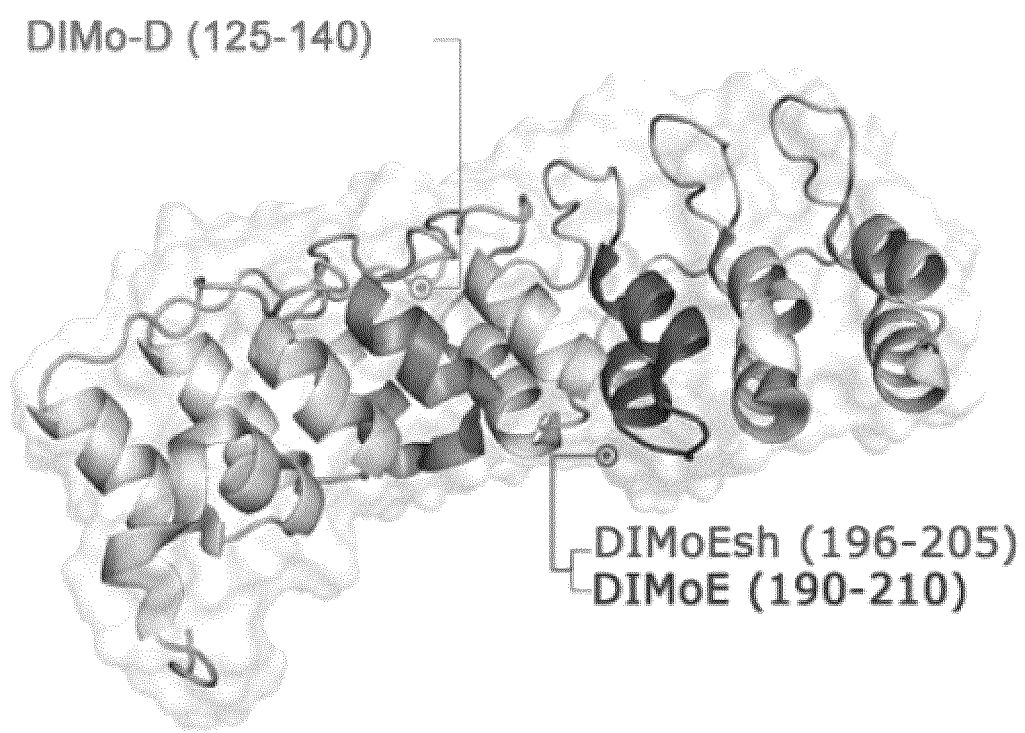
FIG. 6 shows the locations on zD17 from which peptides NIMoD, NIMoE and NIMoEsh are derived, shown in a simulated structure of zD17 ankyrin repeats. 3D structure data was obtained from National Center for Biotechnology Information (PDB: 3EU9) and processed with PyMOL software (v1.3).
Figure 7:
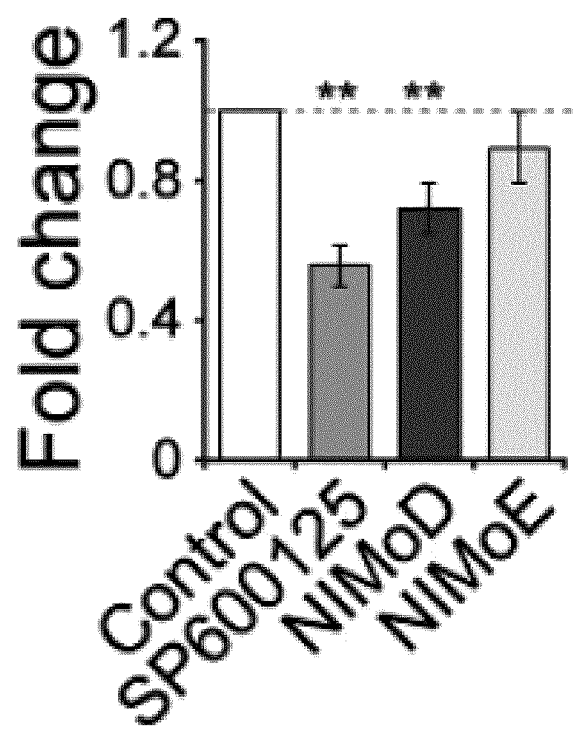
FIG. 7 shows the effect of peptides on JNK3 basal activity. JNK3 was immunoprecipitated from cell lysates, followed by the detection of kinase activity with a kinase assay (KA). Pretreatment of cells with a known JNK inhibitor SP600125 (10 μM) or NIMoD (1 μM) for 2 h caused a significant (fold change to control, 0.56±0.06) or partial (0.72±0.07) reduction of JNK basal activity, respectively. NIMoE (1 μM) has no significant impact on basal activity of JNK3 (0.89±0.10, P=0.33).
Figure 8:
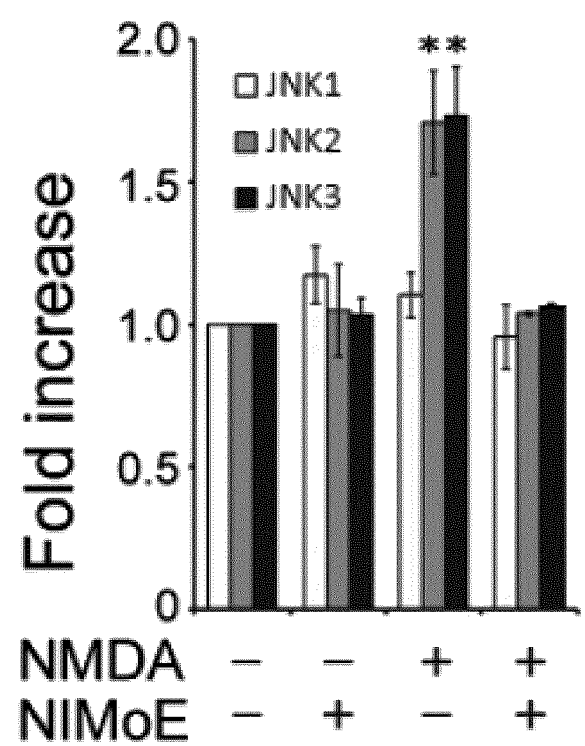
FIG. 8 shows the effect of the peptide NIMoE on the zD17-JNK1/2/3 interaction.
Figure 9:
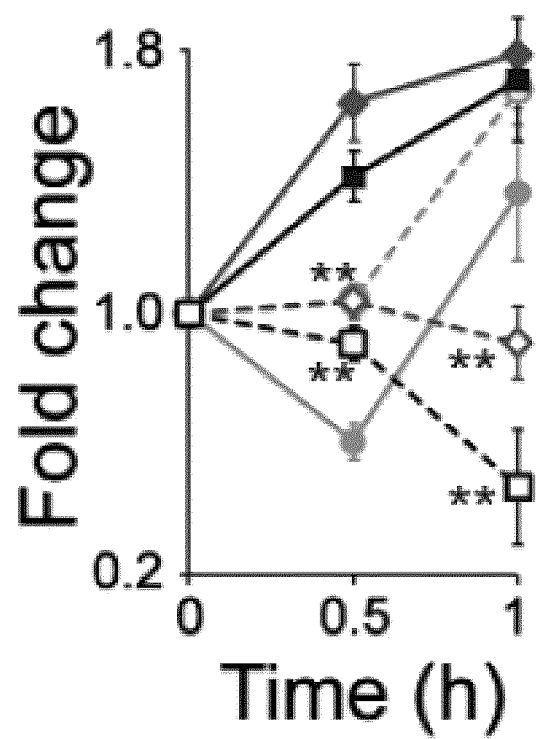
FIG. 9 shows that NIMoE abolishes NMDA-induced activation of JNK2 and JNK3 but not JNK1. JNK is immunoprecipitated from the cell lysate, followed by the determination of JNK activity by kinase assays (KA) (normalized to 0 h. JNK1 (•): 0.5 h, 61.0±5.4%, 1 h, 137.8±20.8%; JNK1+NIMoE (○): 0.5 h, 104.3±2.6, 1 h, 168.5±3.3%; JNK2 (♦): 0.5 h, 164.3±11.5%; 1 h, 179.2±11.2%; JNK2+NIMoE (◇): 0.5 h, 103.7±5.0%; 1 h, 90.9±10.9%; JNK3 (■): 0.5 h, 141.7±7.8%; 1 h, 172.1±18.9%; JNK3+NIMoE (□): 0.5 h, 90.6±5.3%; 1 h, 47.0±17.6%). t-test.  indicates P<0.01. Line graphs show means±s.e.m

Next, it was determined whether targeting these two motifs could inhibit the excitotoxicity-induced zD17-JNK interaction and JNK activation. Peptides comprising motif-D (TPLHWATRGGHLSMV; Novel Interaction Motif D/NIMoD; SEQ ID NO:3) and motif-E (MTPLMWAAYRTHSVDPTRLL; NIMoE; SEQ ID NO:1) were synthesized and fused to the cell-membrane transduction domain of the HIV-1 Tat protein to allow the peptides to penetrate the cell-membrane (Schwarze et al., 1999). Based on results from the peptide array, we optimized NIMoE into a shorter 10mer peptide (WAAYRTHSVD, NIMoEsh; SEQ ID NO:2) which included primarily the loop region of motif-E (zD17196-205) (FIG. 6). BLAST searches showed that the sequence of NIMoE/NIMoEsh is found only within zD17 (data not shown), which supports the specificity findings for these peptides. The application of NIMoD to neuronal cultures significantly diminished the co-immunoprecipitation of zD17 with JNK3, resulting in a reduction of JNK3 basal activity (data not shown). NIMoE showed no effect on the baseline of the zD17-JNK3 interaction and JNK3 activity, but NIMoE selectively blocked the enhancement of the interaction and of JNK3 activity induced by NMDA (data not shown). The negative controls NIMoEscr (HRYRWLTDLLSMVTTPAAPM—a negative control peptide resulting from a scrambled NIMoE—SEQ ID NO:11) and NIMoEmut (MTPLMWAAYGTGSVGPTRLL—a control peptide wherein the NIMoE sequence with point mutations on three charged amino acids (at positions 10, 12, and 15 in bold)—SEQ ID NO:12) did not selectively block enhancement of the interaction and of JNK3 activity induced by NMDA. It also eliminated the enhancement of the JNK2-zD17 interaction and JNK2 activity (FIGS. 8 and 9). In contrast, NIMoE did not inhibit the normal activation of JNK1 (FIG. 9).

Figure 10:
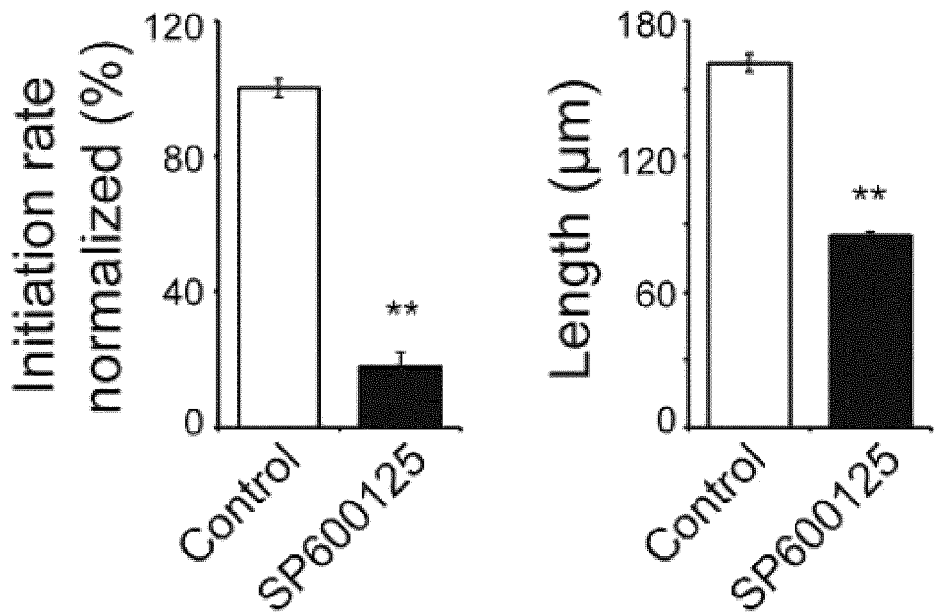
FIG. 10 shows axonal development with peptide application. A, Incubation with SP600125 affects axon initiation and extension. Axons were labelled with the axon marker Tau-1. Axon initiation rate (normalized to control, SP600125, 18.2±4.1%, n=3) and axon length (control, 161.2±3.9; SP600125, 84.9±1.6%, n=4) are shown. B, NIMoE does not block axon initiation (normalized to control, NIMoE, 98.6±0.2%, n=3, P=0.69) or extension (control, 160.0±8.9; NIMoE, 161.1±13.6, n=3; P=0.96). t-test.  indicates P<0.01. Error bars show means±s.e.m.
Figure 10:
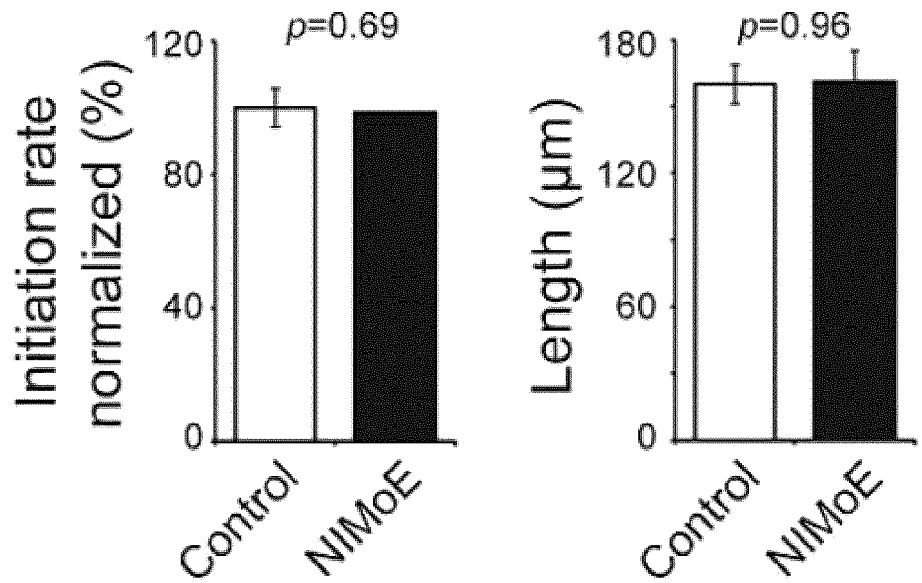

One concern with the use of pan-JNK inhibitors as therapeutics is the non-selective inhibition of JNK1, which is important for normal neuronal development (Oliva et al., 2006). Accordingly, the effect of NIMoE on axonal development was compared to inhibition by the pan-JNK inhibitor SP600125. FIG. 10A shows a comparison of pan-JNK inhibitor SP600125 with a control for axon initiation rate (normalized to control, SP600125, 18.2±4.1%, n=3) and axon length (control, 161.2±3.9; SP600125, 84.9±1.6%, n=4). FIG. 10B shows that chronic incubation with NIMoE in cultured neurons did not affect axon initiation and extension. The results shown in FIGS. 10A and 10B are a quantification of axonal micrographs, where the axons were labelled with the axon marker Tau-1 (micrographs no shown).

Example 5

Neurons are Protected from Excitotoxicity by Targeting the zD17-JNK

Figure 11:
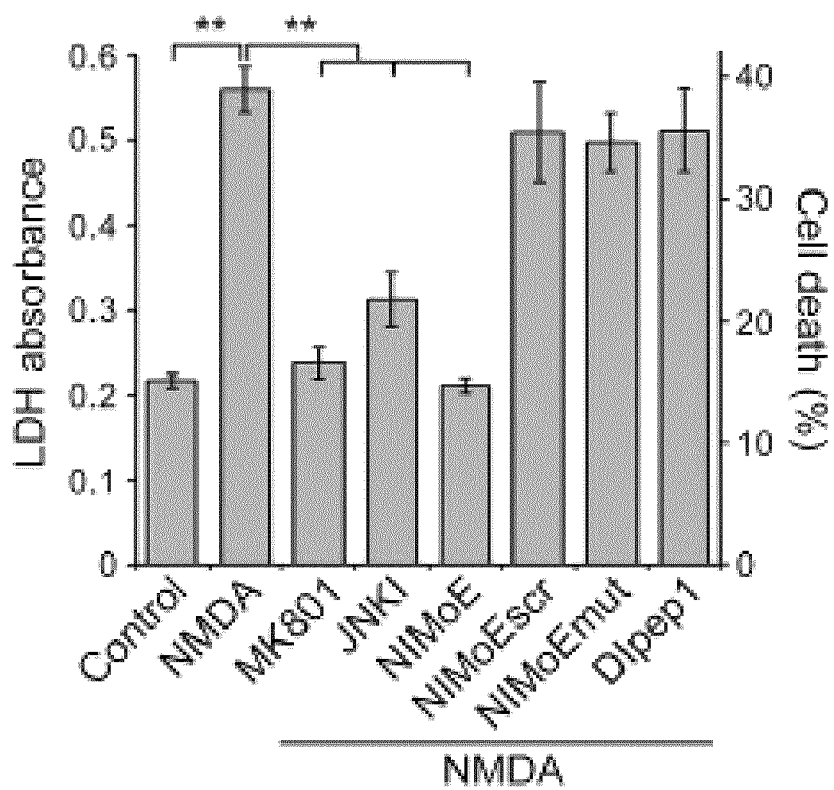
FIG. 11 shows a bar graph of percent NMDA excitotoxicity-induced neuronal cell death based on an LDH assay, which shows the effect of NIMoE, where phase contrast images, PI staining and nuclear Hoechst staining were scored for the integrity of neurites and the shape of nucleus (not shown).
Figure 12:
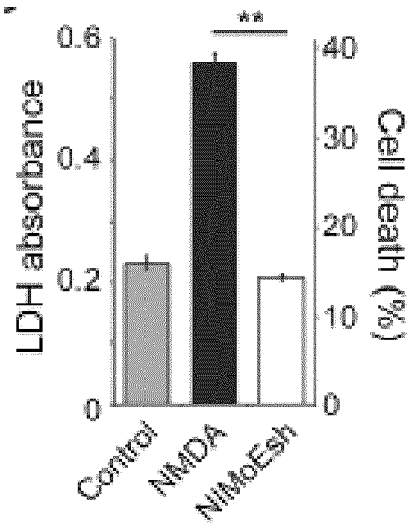
FIG. 12A shows a bar graph quantifying LDH release in NIMoEsh protected cultures as a representation of cell death.
FIG. 12B shows a bar graph quantifying LDH release (to quantify cell death) in NMDA-challenged neuronal cultures at various doses of NIMoE with indicated dosages.
FIG. 12C shows the percent cell death at various NMDA concentrations for NIMoE treated cells (+NIMoE open bars) and NIMoE un-treated cells (−NIMoE shaded bars), whereby NIMoE protects neuronal cultures against a range of NMDA concentrations as indicated. t-test. * and ** indicates P<0.05 and P<0.01, respectively. Error bars show means±s.e.m.
Figure 12:
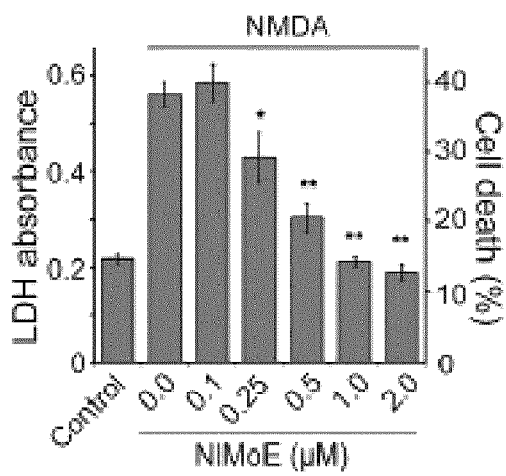
Figure 12:
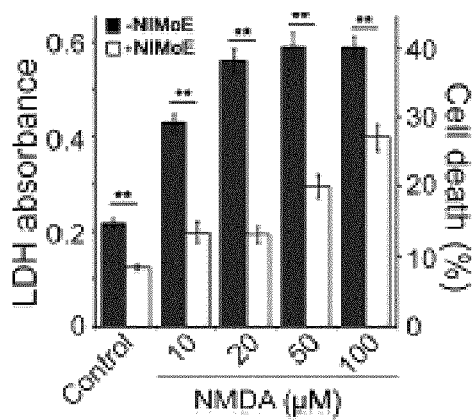

JNK activation is critical for excitotoxicity-induced neuronal death (Centeno et al., 2007). The application of excitotoxic NMDA causes degeneration of neurites, nuclear condensation, membrane permeabilization, and lactate dehydrogenase (LDH) release in neuronal cultures (FIG. 11). Pretreatment with NIMoE or NIMoEsh effectively preserved neuron morphology and significantly prevented excitotoxicity-induced cell death as measured by LDH release and propidium iodide (PI) staining, whereas NIMoEscr, NIMoEmut and a control peptide derived from an unrelated region of zD17 (255NVKGESALDLAKQ267; DIPep1 SEQ ID NO:10) showed no protective effects in neuronal cultures (FIG. 11 and FIGS. 12 A-C). NIMoE also protected neurons against a broad range of NMDA concentrations (10 μM to 100 μM) (FIG. 12C).

Figure 13:
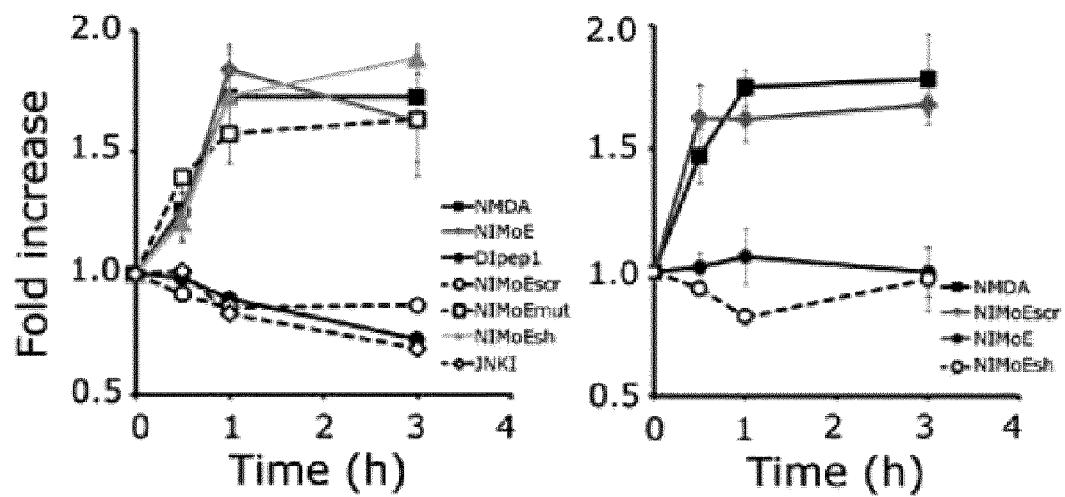
FIG. 13 shows a line graph of c-Jun phosphorylation (left graph) and the p17 form is quantified in (right graph) C, NMDA-induced caspase-3 cleavage is blocked by NIMoE (One-way ANOVA-test. * and ** indicate P<0.05 and P<0.01, respectively. Error bars show means±s.e.m).

JNK2/3 activation mediates neuronal death via two major output pathways: by phosphorylating c-jun to facilitate transcription of pro-death genes, and by activating the mitochondrial caspase-3 pathway to induce apoptosis (Weston and Davis, 2007). NIMoE and NIMoEsh were able to prevent NMDA-induced c-jun phosphorylation (FIG. 13). Caspase-3 cleavage was also effectively blocked by NIMoE and NIMoEsh, while control peptides had no effect (FIG. 13). JNK-mediated caspase-3 cleavage depends on translocation of the pro-apoptotic protein Bax to mitochondria and subsequent release of cytochrome c (Cyt.c) (Tsuruta et al., 2004). NMDA-induced translocation of both Bax and Cyt.c was inhibited by NIMoE and NIMoEsh (data not shown).

Example 6

Targeting the zD17-JNK Module Protects Brains from Ischemic Stroke

Figure 14:
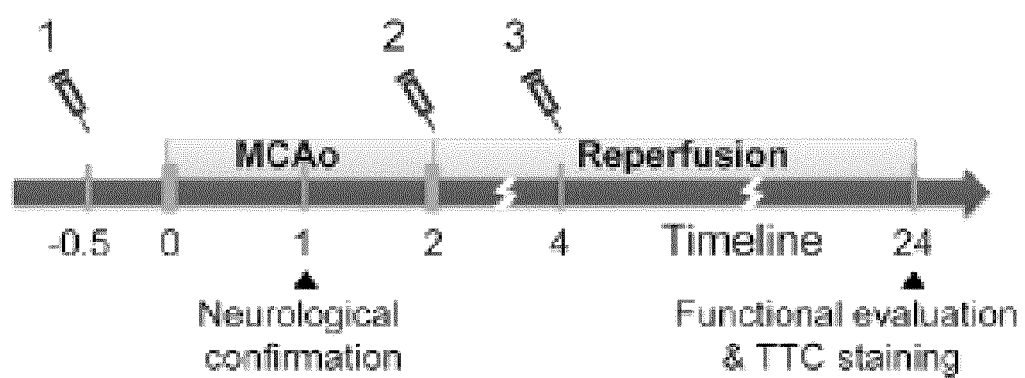
FIG. 14 shows a diagram of the procedures for MCAo experiments in SD rats received sham (control), saline, NIMoEscr, or NIMoEsh by a single i.v. injection at indicated time before or after the onset of ischemia.
Figure 15:
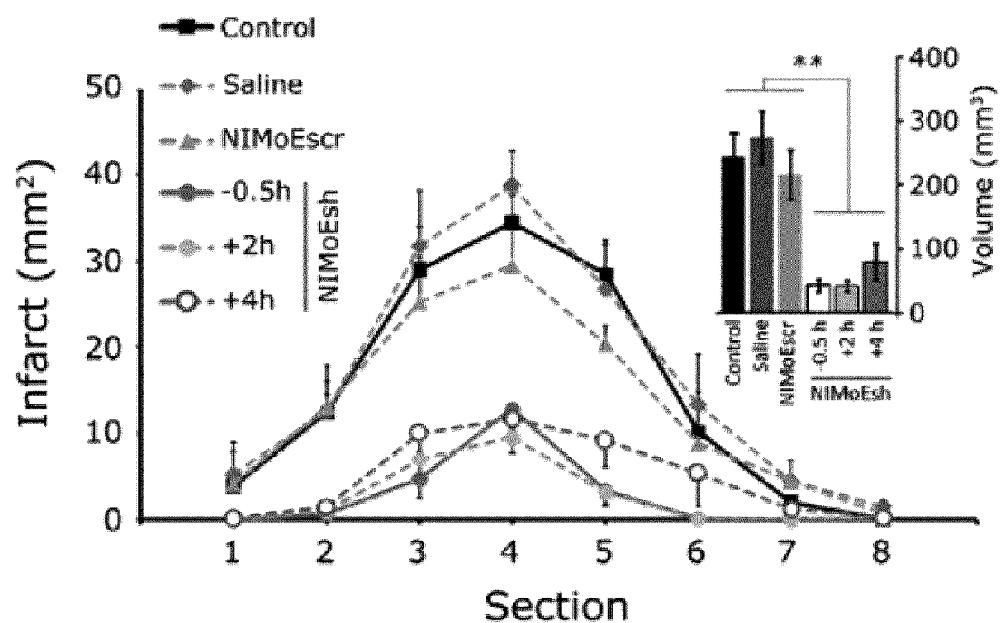
FIG. 15 shows two graphs that quantify the total infarct size and volume (inset bar-chart), where the NIMoEsh treatments (−0.5 h, 43.43±9.82, n=7; +2 h, 41.95±8.22, n=10; +4 h, 78.74±28.50, n=6; F=20.71, P<0.01 compared with control groups) dramatically reduced total infarct volume, while saline or NIMoEscr had little effect (control, 240.70±35.67, n=9; saline, 268.89±40.47, n=4; NIMoEscr, 212.60±37.6, n=5; F=0.38, P=0.69) (One-way ANOVA-test).
Figure 16:
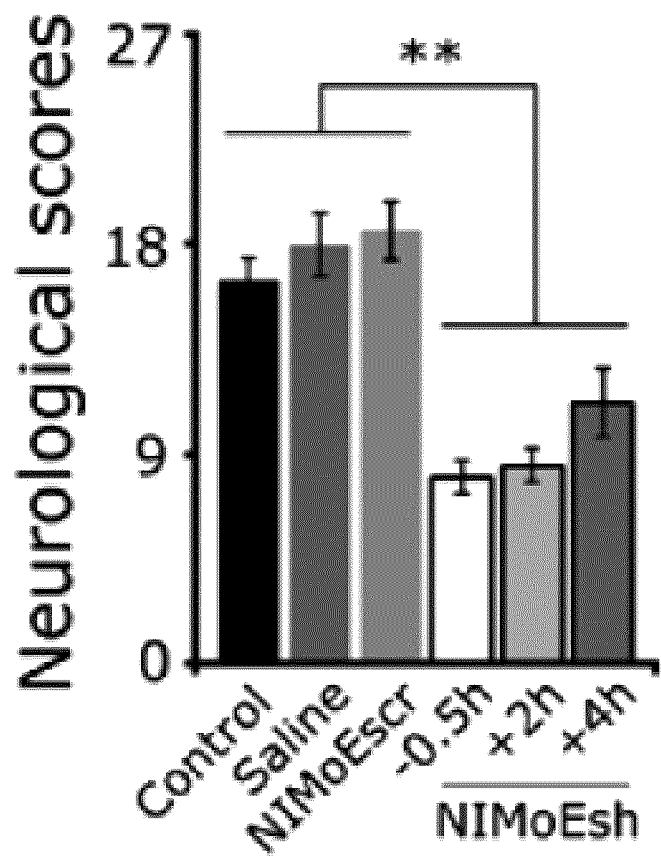
FIG. 16 shows a bar graph representing neurological scores that indicate an improved behavioural outcome in ischemic rats treated with NIMoEsh. Neurological functions were examined 22 h after the onset of MCAo. Saline or NIMoEscr treated groups showed similar deficits (control, 16.43±0.95, n=7; saline, 18.00±1.35, n=4; NIMoEscr, 18.60±1.24, n=5; F=1.65, P=0.23). Administration of NIMoEsh significantly reduced neurological scores (−0.5 h, 8.00±0.72, n=7; +2 h, 8.50±0.75, n=10; +4 h, 11.20±1.49, n=6; F=21.98, P<0.01 compared with control groups). One-way ANOVA-test.
Figure 17:
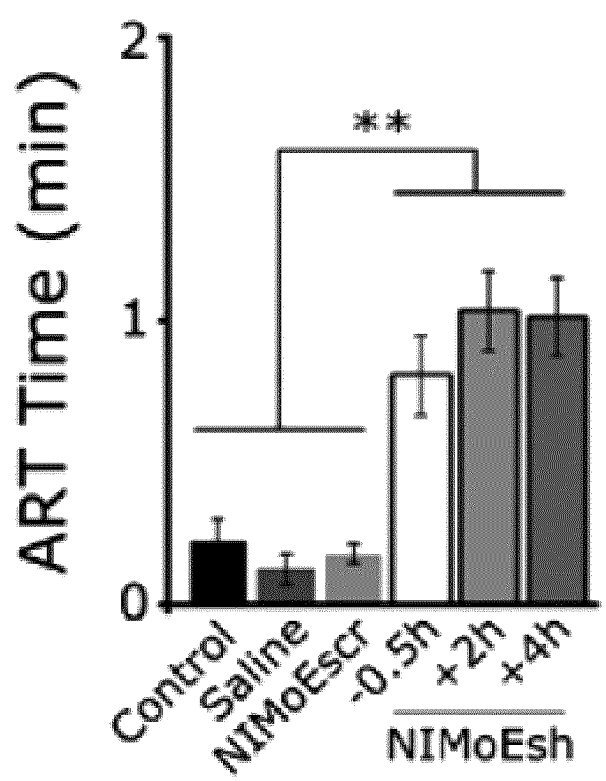
FIG. 17 shows a bar graph of somatosensory functions as assessed with the adhesive removal test (ART) and shows NIMoE treatment improves ART scores. MCAo eliminates responses on the contralateral side in control, saline-treated and NIMoEscr-treated animals (control, 13.57±4.30 sec, n=7; saline, 7.42±3.21 sec, n=4; NIMoEscr, 10.80±2.06 sec, n=5; F=0.64, P=0.54). Pre-treatment or post-treatment infusion of NIMoE led to an improvement in somatosensory functions (−0.5 h, 48.62±8.24 sec, n=7; +2 h, 62.1±8.60 sec, n=10; +4 h, 60.83±8.13 sec, n=6; F=11.28, P<0.01). One-way ANOVA-test.
Figure 18:
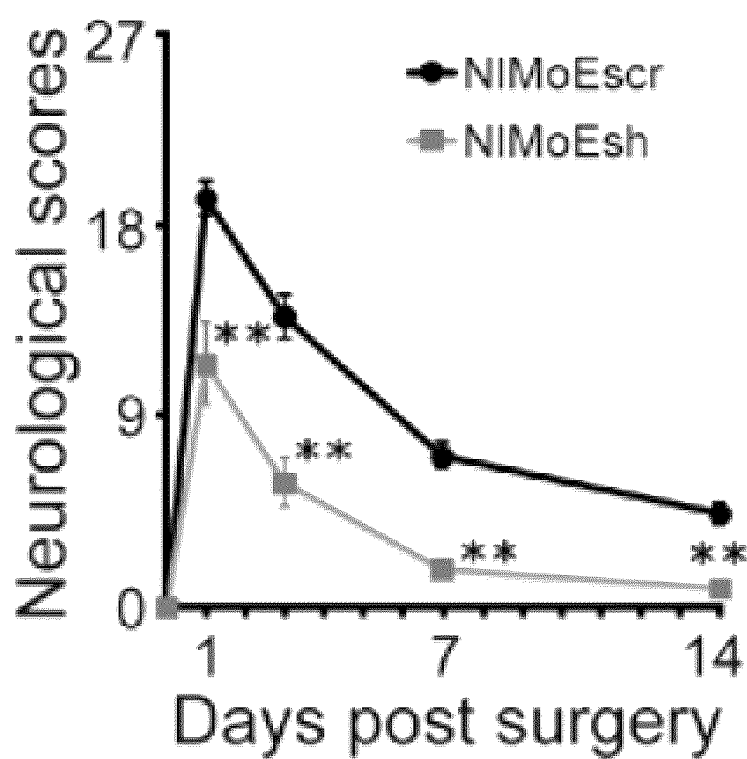
FIGS. 18 and 19 show a line graphs for functional tests and show improved behavioural outcomes in NIMoEsh-treated animals after MCAo injury. NIMoEscr or NIMoEsh were given 4 h after the MCAo onset. Neurological scores (NIMoEscr, n=8; day-1, 19.25±0.80; day-3, 13.63±1.03; day-7, 7.13±0.58; day-14, 4.38±0.50; NIMoEsh, n=7; day-1, 11.43±1.96; day-3, 5.86±1.14; day-7, 1.71±0.47; day-14, 0.85±0.34) and ART (NIMoEscr, n=8; day-1, 12.63±3.14; day-3, 34.13±6.88; day-7, 59.13±5.67; day-14, 81.88±4.44; NIMoEsh, n=7; day-1, 52.57±6.82; day-3, 73.86±9.63; day-7, 94.86±7.33; day-14, 101.43±3.35). t-test. ** indicates P<0.01. Error bars show means±s.e.m.
Figure 19:
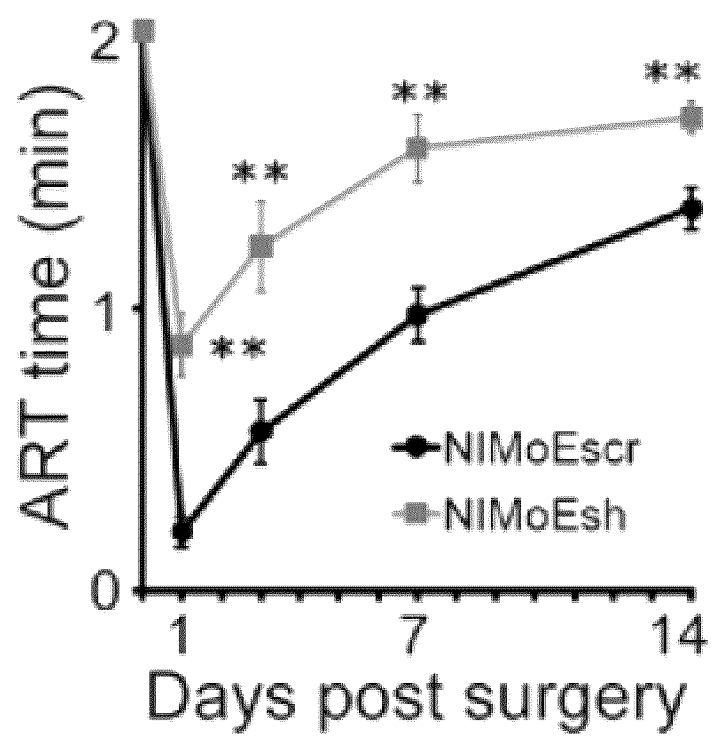

The strategy was applied in vivo in a model of transient ischemic stroke (Longa et al., 1989). Adult male Sprague-Dawley rats were subjected to left middle cerebral artery occlusion (MCAo) for 2 h, followed by 22 h reperfusion (FIG. 14). The zD17-JNK3 interaction in the injured hemisphere (L) remained enhanced up to at least 6 h after the ischemic insult, implying a broad time window for potential intervention. A shorter form of the NIMoE peptide (i.e. NIMoEsh) was used in the in vivo experiments. A single intravenous injection of NIMoEsh 30 min before MCAo effectively attenuated the enhancement of the zD17-JNK3 interaction, and dramatically reduced the total infarct size (by about 80%; FIG. 15). The effects of post-surgical interventions at 2 h or 4 h were also assessed. Compared with the infarct volume of non-treated, saline-treated, and scramble peptide-treated groups, NIMoEsh showed effective protection for the ischemic brain (FIG. 15). The behavioural deficits, as evaluated with neurological scores (Bederson et al., 1986; Watanabe et al., 2004) were substantially reduced by NIMoEsh administration (FIG. 16). The quantitative adhesive removal test (ART) further confirmed a large preservation of somatosensory functions in NIMoEsh-treated rats (FIG. 17) (Bouet et al., 2009). The improvement of behavioural performance persisted over 14 days in ischemic rats injected with NIMoEsh 2 h post-surgery, assessed in a double-blinded manner (FIGS. 18 and 19). Together, these results suggest that targeting the zD17-JNK module to prevent JNK activation is effective in protecting the brain from ischemic injury and in improving behavioural outcomes.

Herein it is demonstrated that targeting a novel and specific NMDA-induced interaction between two proteins can confer effective neuroprotection against NMDA-induced excitotoxicity in vitro and ischemic stroke in vivo. In vivo, robust neuroprotection was still observed even when the blocking peptide was given 6 h after MCAo onset.

The multiple functions and diverse palmitoylation substrates of zD17 indicate a complex role in brain function and toxicity. The strategy employed herein does not interfere with zD17 itself or its constitutive functions. Rather, using motif-derived peptides, it has been demonstrated that zD17 is a JNK interaction partner and that their interaction is dynamically regulated by neuronal stressors. zD17 binds all JNK isoforms, but it displays specificity for JNK2/3 under neurotoxic conditions via a novel motif (motif-E), that is different from previous known JNK-interacting motifs. With the selectivity for JNK2/3, this motif provides a novel and selective neuroprotective target for therapeutic intervention.

The regulatory mechanisms for this zD17-JNK signaling module include zD17 interactions with its substrate, PSD-95, by way of substrate palmitoylation. In excitotoxicity, PSD-95 is mobilized to NR2B and becomes less available to zD17, thus enhancing zD17's interaction with JNK. The foregoing highlights zD17 as a hub protein, which senses its substrates and recruits other proteins, including MKK7, to the signaling module to generate output to JNK pathways. Altered palmitoylation and interaction profiles of zD17 substrates have been noted in several neurological diseases (see, for e.g.: Yanai et al., 2006; El-Husseini Ad et al., 2002; and Kornau et al., 1995), the zD17-JNK signaling module may also contribute to pathological JNK activation and neuronal death in these conditions. Based on the peptide blockers' efficacy in treating ischemic stroke as shown herein, blocking the zD17-JNK interaction may be a therapeutic strategy in other conditions leading to neuronal toxicity.

While specific embodiments of the invention have been described and illustrated, such embodiments should be considered illustrative of the invention only and not as limiting the invention as construed in accordance with the accompanying claims. Other features and advantages of the invention will be apparent from the following description of the drawings and the invention, and from the claims.

INFORMAL SEQUENCE LISTING

SEQ ID NO: 1
(also referred to herein as NIMoE): MTPLMWAAYRTHSVDPTRLL.

SEQ ID NO: 2
(also referred to as NIMoEsh): WAAYRTHSVD.

SEQ ID NO: 3
(also referred to as NIMoD): TPLHWATRGGHLSMV.

SEQ ID NO: 4
(NIMoE conjugated to TAT protein transduction domain (aa 21-31)):
MTPLMWAAYRTHSVDPTRLL-YGRKKRRQRRR.

SEQ ID NO: 5
(NIMoEsh conjugated to TAT protein transduction domain (aa 11-21)):
WAAYRTHSVD-YGRKKRRQRRR.

SEQ ID NO: 6
(NIMoD conjugated to TAT protein transduction domain (aa 16-26)):
TPLHWATRGGHLSMV-YGRKKRRQRRR.

INFORMAL SEQUENCE LISTING

SEQ ID NO: 7
(NIMoE conjugated to TAT protein transduction domain (aa 1-11)):
YGRKKRRQRRR-MTPLMWAAYRTHSVDPTRLL.

SEQ ID NO: 8
(NIMoEsh conjugated to TAT protein transduction domain (aa 1-11)):
YGRKKRRQRRR-WAAYRTHSVD.

SEQ ID NO: 9
(NIMoD conjugated to TAT protein transduction domain (aa 1-11)):
YGRKKRRQRRR-TPLHWATRGGHLSMV.

SEQ ID NO: 10
(DIPep1 a control peptide derived from an unrelated region of zD17 (255-267)): NVKGESALDLAKQ.

SEQ ID NO: 11
(NIMoEscr a control peptide resulting from a scrambled NIMoE):
HRYRWLTDLLSMVTTPAAPM.

SEQ ID NO: 12
(NIMoEmut a control peptide wherein the NIMoE sequence with point mutations on three charged amino acids (at positions 10, 12, and 15 in bold)): MTPLMWAAYGTGSVGPTRLL.

SEQ ID NO: 13
(NIMoEscr a control peptide resulting from a scrambled NIMoE which is conjugated to TAT protein transduction domain (aa 1-11)):
YGRKKRRQRRR-HRYRWLTDLLSMVTTPAAPM.

SEQ ID NO: 14
(NIMoEmut a control peptide wherein the NIMoE sequence with point mutations on three charged amino acids (positions 21, 23, and 26 in bold) is conjugated to TAT protein transduction domain (aa 1-11)):
YGRKKRRQRRR-MTPLMWAAYGTGSVGPTRLL.

We claim:

1. An isolated polypeptide consisting of (a) one of: SEQ ID NO:1; or (b) a fragment of SEQ ID NO:1 wherein that fragment comprises SEQ ID NO:2; wherein the isolated polypeptide inhibits an interaction between palmitoyl acyl transferase zinc-finger DHHC type containing 17 (zD17) and c-jun N-terminal kinase (JNK), and wherein the isolated polypeptide is conjugated to a protein transduction domain.

2. The isolated polypeptide of claim 1, wherein the protein transduction domain is the cell-membrane transduction domain of the HIV-1 Tat protein.

3. A method of protecting a cell from excitotoxic stress, the method comprising; delivering an isolated polypeptide of claim 1 to the cell.

4. A method of treating a disease associated with excitotoxicity, the method comprising: administering a biologically effective amount of the polypeptide of claim 1 to a subject in need thereof.

5. The method of claim 4, wherein the biologically effective amount is an amount sufficient to prevent excitotoxicity-induced cell death.

6. The method of claim 4, wherein the disease associated with excitotoxicity is selected from spinal cord injury, stroke, brain injury, multiple sclerosis, Alzheimer's disease, amyotrophic lateral sclerosis (ALS), Parkinson's disease, alcoholism or alcohol withdrawal, and Huntington's disease.

7. A vector comprising an isolated polynucleotide, comprising a series of nucleotides encoding a polypeptide consisting of (a) SEQ ID NO:1; or (b) a fragment of SEQ ID NO:1 wherein that fragment comprises SEQ ID NO:2; wherein the isolated polypeptide inhibits an interaction between palmitoyl acyl transferase zinc-finger DHHC type containing 17 (zD17) and c-jun N-terminal kinase (JNK), and wherein the isolated polypeptide is conjugated to a protein transduction domain.

8. The vector of claim 7, wherein the vector is within a cell.

9. The vector of claim 7, wherein the polynucleotide is operably linked to an expression control sequence.

10. A method of protecting a cell from excitotoxic stress, the method comprising: (a) delivering the vector of claim 7 to the cell; and (b) expressing the polynucleotide carried by the vector.

11. A pharmaceutical composition comprising:
   (a) an isolated polypeptide consisting of (i) SEQ ID NO:1; or (ii) a fragment of SEQ ID NO:1 wherein that fragment comprises SEQ ID NO:2; wherein the isolated polypeptide inhibits an interaction between palmitoyl acyl transferase zinc-finger DHHC type containing 17 (zD17) and c-jun N-terminal kinase (JNK); and wherein the isolated polypeptide is conjugated to a protein transduction domain; and
   (b) a pharmaceutically acceptable excipient.

12. The composition of claim 11, wherein the excipient is an isotonic injection solution.

13. The composition of claim 11, wherein the composition is suitable for human administration.

14. The composition of claim 11, wherein the protein transduction domain is a cell-membrane transduction domain of the HIV-1 Tat protein.

* * * * *

UNITED STATES PATENT AND TRADEMARK OFFICE
CERTIFICATE OF CORRECTION

| | | |
|---|---|---|
| PATENT NO. | : 9,458,437 B2 | Page 1 of 1 |
| APPLICATION NO. | : 14/232268 | |
| DATED | : October 4, 2016 | |
| INVENTOR(S) | : Cynader | |

It is certified that error appears in the above-identified patent and that said Letters Patent is hereby corrected as shown below:

In the Claims

Claim 1, Column 33 Line 25, "one of:" should be deleted.

Claim 3, Column 33 Line 36, "comprising;" should be deleted and insert -- comprising: --.

Signed and Sealed this
Twenty-first Day of February, 2017

Michelle K. Lee
*Director of the United States Patent and Trademark Office*